United States Patent
Lankhof et al.

(10) Patent No.: US 10,123,920 B2
(45) Date of Patent: Nov. 13, 2018

(54) ABSORBENT ARTICLE HAVING ASYMMETRIC ABSORBENT CORE COMPONENT

(75) Inventors: John Peter Lankhof, Schmitten (DE); Yukio Heki, Kobe (JP); Masahiro Kondo, Kobe (JP); Niels Hollenberg, Schwalbach (DE); Steven Stuart Bullock, Loveland, OH (US); Toshiyuki Iwata, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 1877 days.

(21) Appl. No.: 11/506,387

(22) Filed: Aug. 18, 2006

(65) Prior Publication Data

US 2007/0043330 A1 Feb. 22, 2007

Related U.S. Application Data

(60) Provisional application No. 60/710,032, filed on Aug. 19, 2005, provisional application No. 60/818,109, filed on Jun. 30, 2006.

(51) Int. Cl.

| | |
|---|---|
| *A61F 13/535* | (2006.01) |
| *A61F 13/84* | (2006.01) |
| *A61F 13/531* | (2006.01) |
| *A61L 15/28* | (2006.01) |
| *A61F 13/47* | (2006.01) |

(Continued)

(52) U.S. Cl.
CPC .......... *A61F 13/84* (2013.01); *A61F 13/4704* (2013.01); *A61F 13/51394* (2013.01); *A61F 13/531* (2013.01); *A61F 13/535* (2013.01); *A61F 13/53713* (2013.01); *A61F 13/53756* (2013.01); *A61F 13/5611* (2013.01); *A61L 15/28* (2013.01); *A61F 2013/1539* (2013.01);

(Continued)

(58) Field of Classification Search
CPC .................. A61F 13/535; A61F 2013/5355
See application file for complete search history.

(56) References Cited

U.S. PATENT DOCUMENTS 3,667,468 A * 6/1972 Nystrand et al. ............. 604/380
3,814,100 A * 6/1974 Nystrand et al. ............. 604/390

(Continued)

FOREIGN PATENT DOCUMENTS

| JP | 9-266928 | 10/1997 |
|---|---|---|
| WO | WO 03/017900 A1 | 3/2003 |

(Continued)

OTHER PUBLICATIONS

International Search Report dated Dec. 21, 2006.
PCT International Search Report dated Dec. 21, 2006.

*Primary Examiner* — Paula L Craig
(74) *Attorney, Agent, or Firm* — Andres Ernesto Velarde; Amanda T. Barry

(57) ABSTRACT

An absorbent article for wearing about the lower torso of a wearer includes a topsheet, a backsheet joined to at least a portion of the topsheet, and an absorbent core disposed between the topsheet and the backsheet. The absorbent core includes a first layer and a second layer, wherein the first layer is disposed in fluid communication with the second layer. The first layer has a first shape and the second layer has a second shape. The first shape is different from the second shape. Each of the first layer and second layer comprise less than about 20 percent airfelt.

11 Claims, 30 Drawing Sheets

(51) Int. Cl.
  *A61F 13/513* (2006.01)
  *A61F 13/537* (2006.01)
  *A61F 13/56* (2006.01)
  *A61F 13/15* (2006.01)
  *A61F 13/51* (2006.01)

(52) U.S. Cl.
  CPC ............... A61F 2013/51026 (2013.01); A61F 2013/5315 (2013.01)

(56) References Cited

U.S. PATENT DOCUMENTS

| | | | |
|---|---|---|---|
| 3,865,111 A * | 2/1975 | Brooks | 604/378 |
| 4,055,180 A * | 10/1977 | Karami | 604/368 |
| 4,100,324 A * | 7/1978 | Anderson | C11D 17/049 156/167 |
| 4,146,417 A * | 3/1979 | Drelich | D04H 1/64 156/181 |
| 4,195,634 A * | 4/1980 | DiSalvo | A61F 13/4702 604/359 |
| 4,327,728 A * | 5/1982 | Elias | 604/368 |
| 4,551,143 A * | 11/1985 | Cook | A61F 13/513 604/367 |
| 4,556,146 A * | 12/1985 | Swanson | A61F 13/5514 206/438 |
| 4,578,068 A * | 3/1986 | Kramer et al. | 604/368 |
| 4,670,011 A * | 6/1987 | Mesek | 604/378 |
| 4,770,657 A * | 9/1988 | Ellis | A61F 13/4752 604/370 |
| 4,781,711 A * | 11/1988 | Houghton et al. | 604/378 |
| RE32,957 E * | 6/1989 | Elias et al. | 604/368 |
| 4,865,597 A * | 9/1989 | Mason, Jr. | A61F 13/4702 604/366 |
| 4,880,419 A * | 11/1989 | Ness | 604/368 |
| 4,888,231 A * | 12/1989 | Angstadt | 428/213 |
| 4,960,477 A * | 10/1990 | Mesek | 156/209 |
| 4,988,344 A * | 1/1991 | Reising et al. | 604/368 |
| 5,217,445 A * | 6/1993 | Young et al. | 604/381 |
| 5,246,772 A * | 9/1993 | Manning | B32B 5/12 442/364 |
| 5,248,309 A * | 9/1993 | Serbiak et al. | 604/368 |
| 5,300,054 A * | 4/1994 | Feist et al. | 604/378 |
| 5,304,161 A * | 4/1994 | Noel et al. | 604/378 |
| 5,382,245 A * | 1/1995 | Thompson et al. | 604/367 |
| 5,387,208 A * | 2/1995 | Ashton et al. | 604/378 |
| 5,411,497 A * | 5/1995 | Tenzer et al. | 604/368 |
| 5,413,568 A * | 5/1995 | Roach | A61F 13/5514 206/440 |
| 5,439,458 A | 8/1995 | Noel et al. | |
| 5,527,303 A * | 6/1996 | Milby et al. | 604/385.16 |
| 5,562,646 A * | 10/1996 | Goldman et al. | 604/368 |
| 5,591,149 A | 1/1997 | Cree et al. | |
| 5,593,399 A * | 1/1997 | Tenzer et al. | 604/368 |
| 5,601,542 A * | 2/1997 | Melius et al. | 604/368 |
| 5,624,423 A * | 4/1997 | Anjur | A61F 13/4757 604/369 |
| 5,643,238 A * | 7/1997 | Baker | 604/368 |
| 5,681,300 A | 10/1997 | Ahr et al. | |
| 5,704,931 A * | 1/1998 | Holtman | A61F 13/45 604/385.01 |
| 5,756,039 A * | 5/1998 | McFall et al. | 264/517 |
| 5,762,641 A | 6/1998 | Bewick-Sonntag et al. | |
| 5,817,081 A * | 10/1998 | LaVon et al. | 604/378 |
| 5,820,973 A * | 10/1998 | Dodge, II | A61F 13/15203 428/212 |
| 5,830,202 A * | 11/1998 | Bogdanski et al. | 604/378 |
| 5,836,929 A | 11/1998 | Bewick-Sonntag et al. | |
| 5,855,572 A * | 1/1999 | Schmidt | 604/378 |
| 5,938,650 A * | 8/1999 | Baer et al. | 604/368 |
| 6,066,775 A * | 5/2000 | Bachar | 604/368 |
| 6,077,895 A * | 6/2000 | Strelow | A61L 15/225 524/272 |
| 6,096,299 A | 8/2000 | Guarracino et al. | |
| 6,103,953 A * | 8/2000 | Cree et al. | 604/365 |
| 6,231,556 B1 | 5/2001 | Osborn, III | |
| 6,315,765 B1 * | 11/2001 | Datta | A61F 13/47272 604/358 |
| 6,316,688 B1 * | 11/2001 | Hammons et al. | 604/378 |
| 6,323,388 B1 * | 11/2001 | Melius et al. | 604/368 |
| 6,326,525 B1 * | 12/2001 | Hamajima et al. | 604/378 |
| 6,372,953 B1 * | 4/2002 | Young | A43B 1/0036 604/369 |
| 6,383,169 B1 * | 5/2002 | Mills | A61F 13/4752 604/385.02 |
| 6,409,883 B1 | 6/2002 | Makolin et al. | |
| 6,425,890 B1 * | 7/2002 | Samuelsson | A61F 13/4702 604/378 |
| 6,455,753 B1 * | 9/2002 | Glaug et al. | 604/383 |
| 6,503,233 B1 | 1/2003 | Chen et al. | |
| 6,562,192 B1 | 5/2003 | Hamilton et al. | |
| 6,572,598 B1 * | 6/2003 | Ashton | A61F 13/49012 604/385.01 |
| 6,610,900 B1 * | 8/2003 | Tanzer | 604/368 |
| 6,645,569 B2 | 11/2003 | Cramer et al. | |
| 6,646,180 B1 * | 11/2003 | Chmielewski | 604/368 |
| 6,667,424 B1 | 12/2003 | Hamilton et al. | |
| 6,673,982 B1 | 1/2004 | Chen et al. | |
| 6,695,827 B2 | 2/2004 | Chen et al. | |
| 6,863,933 B2 | 3/2005 | Cramer et al. | |
| 6,878,433 B2 * | 4/2005 | Curro et al. | 428/198 |
| 6,878,647 B1 * | 4/2005 | Rezai | A61F 13/49012 264/288.8 |
| 6,887,564 B2 | 5/2005 | Gagliardini et al. | |
| 7,122,023 B1 * | 10/2006 | Hinoki | 604/385.101 |
| 7,247,215 B2 * | 7/2007 | Schewe et al. | 156/250 |
| 7,265,258 B2 | 9/2007 | Hamilton et al. | |
| 7,429,689 B2 | 9/2008 | Chen et al. | |
| 7,662,460 B2 | 2/2010 | Herfert et al. | |
| 7,744,576 B2 | 6/2010 | Busam et al. | |
| 2001/0021839 A1 * | 9/2001 | Kashiwagi | A61F 13/47218 604/400 |
| 2002/0009937 A1 * | 1/2002 | Dukes | C08J 3/03 442/156 |
| 2003/0125701 A1 * | 7/2003 | Widlund | A61F 13/4702 604/385.31 |
| 2003/0135177 A1 * | 7/2003 | Baker | 604/368 |
| 2004/0106910 A1 * | 6/2004 | Vercauteren et al. | 604/378 |
| 2004/0121678 A1 * | 6/2004 | Baldwin, Jr. | A41D 13/008 442/110 |
| 2004/0162536 A1 | 8/2004 | Becker et al. | |
| 2004/0167486 A1 | 8/2004 | Busam et al. | |
| 2004/0243081 A1 * | 12/2004 | Suzuki et al. | 604/378 |
| 2005/0059942 A1 * | 3/2005 | Krautkramer et al. | 604/378 |
| 2005/0100713 A1 * | 5/2005 | Busam | D06C 23/04 428/178 |
| 2005/0153123 A1 * | 7/2005 | Herfert et al. | 428/327 |
| 2006/0287636 A1 * | 12/2006 | Sakai | A61F 13/4702 604/385.101 |
| 2008/0125735 A1 | 5/2008 | Busam et al. | |
| 2010/0228210 A1 | 9/2010 | Busam et al. | |

FOREIGN PATENT DOCUMENTS

WO  WO 2004/084784 A1  10/2004
WO  WO 2004/084785 A1  10/2004
WO  WO 2005/032443 A1  4/2005

* cited by examiner

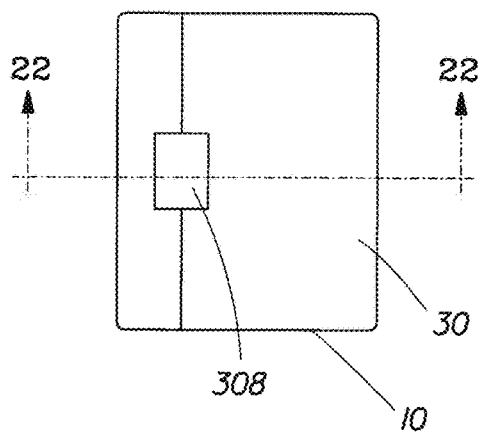
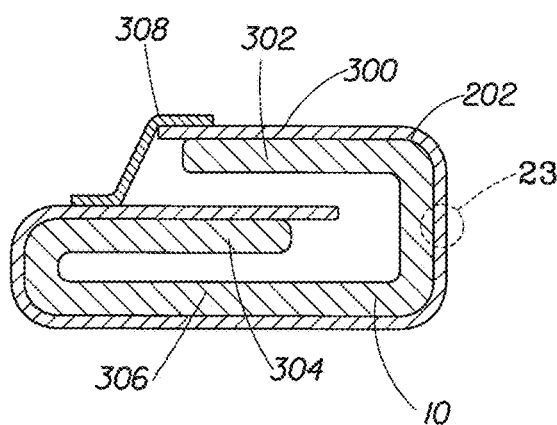
Fig. 21                Fig. 22
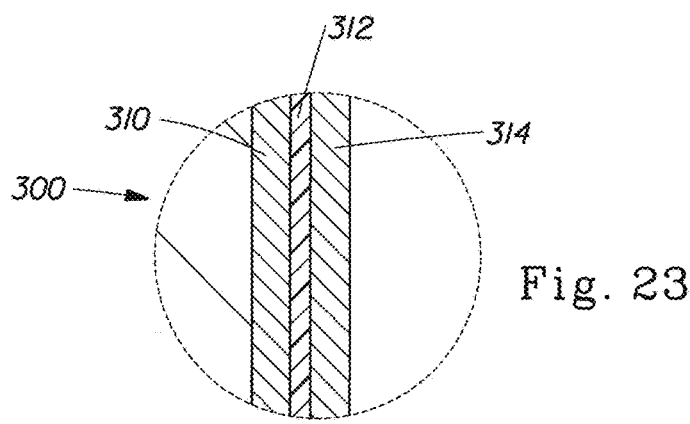
Fig. 23
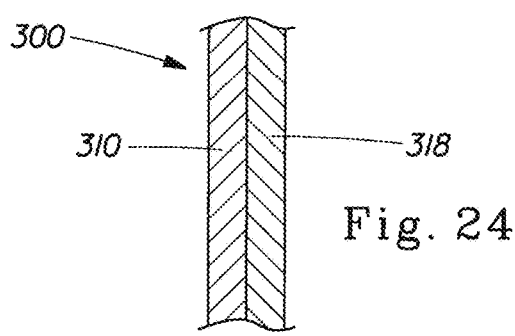
Fig. 24

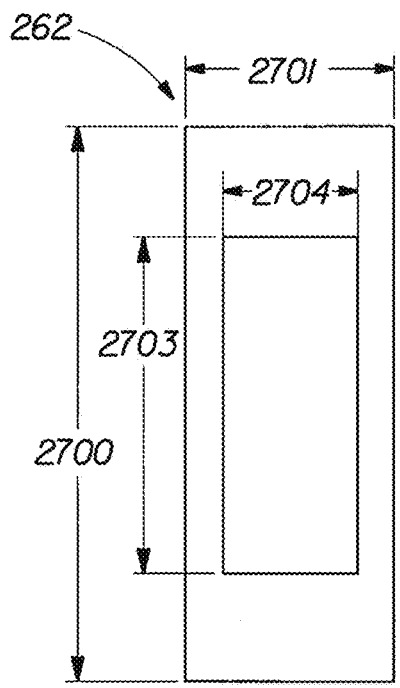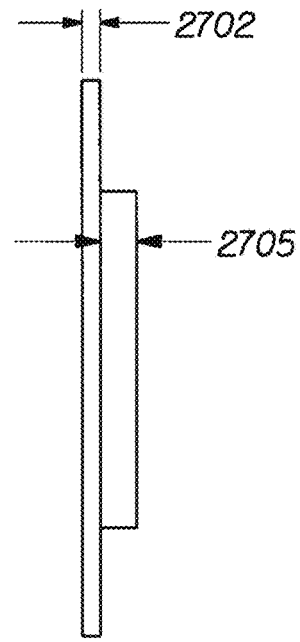
Fig. 28A       Fig. 28B
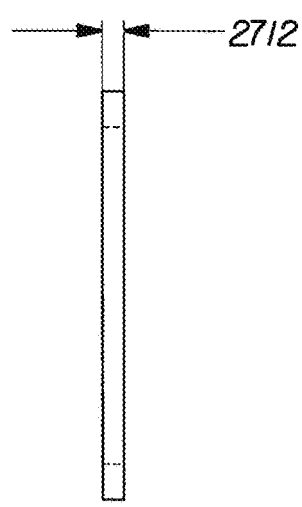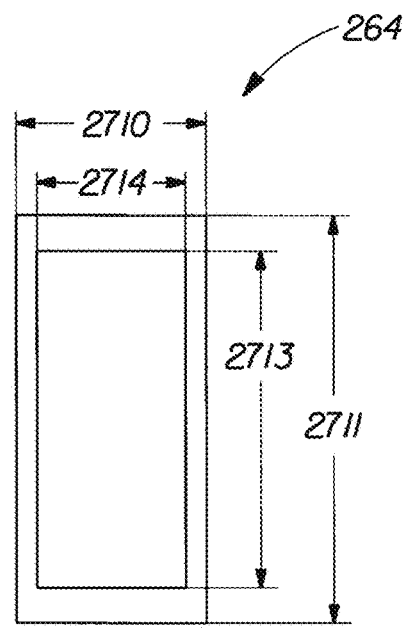
Fig. 28C       Fig. 28D

ABSORBENT ARTICLE HAVING ASYMMETRIC ABSORBENT CORE COMPONENT

CROSS REFERENCE

This application claims the benefit of U.S. Provisional Application Ser. No. 60/710,032 filed on Aug. 19, 2005 and claims the benefit of U.S. Provisional Application Ser. No. 60/818,109 filed on Jun. 30, 2006.

FIELD OF INVENTION

The present application relates generally to absorbent articles and more particularly to a disposable absorbent article, such as an adult incontinence pad.

BACKGROUND

Infants, children and adult incontinent individuals wear disposable personal care absorbent articles such as diapers, training pants, and incontinent briefs, to receive and contain discharged urine and excrement. Disposable personal care absorbent articles such as diapers, training pants, and incontinent briefs, are well known in the art. These disposable personal care absorbent articles can function both to retain the discharged materials and to isolate those materials from the body of the wearer as well as from the garments, clothing and bedding, of the wearer. Generally, such disposable personal care absorbent articles collect and retain urine and excrement including fecal material and any other waste matter discharged from the alimentary canal and deposited thereon by the wearer.

Typical incontinence pads are attached to an inner surface of a garment and fit between legs of a user. Incontinence pads often include a topsheet which faces towards and contacts the body of the wearer and a liquid impervious backsheet that is positioned opposite the topsheet. Between the topsheet and the backsheet is an absorbent core. A typical absorbent core includes a relatively thick absorbent structure of a combination of fibrous material such as comminuted wood pulp allowing the topsheet to be drained of liquid that contacts it so that the topsheet may acquire and distribute more liquids. The absorbent core absorbs urine or other liquids and transfers these liquids to a storage area keeping the wearer dry even when the disposable diaper or incontinence pad is removed from the wearer.

Typically, to increase capacity of the absorbent core, the dry volume of the absorbent structure of the absorbent core is increased. A caliper of an absorbent structure may be up to 80 percent of a total dry caliper of the incontinence pad.

It is often desirable to provide incontinence pads having increased capacity to absorb and retain urine and other bodily exudates. In order to increase capacity of the incontinence pads, the dry volume including the thickness of the absorbent core is typically increased. Such an increase in thickness can result in a decrease in a wearer's comfort, thereby inducing the wearer to select a pad that may not possess the absorbency necessary to meet the wearer's needs.

SUMMARY

One embodiment of the present invention features an absorbent article that includes a topsheet, a backsheet joined at least to a portion of the topsheet, and an absorbent core located between the topsheet and the backsheet. The absorbent core comprises a first storage layer and a second storage layer, wherein the first storage layer is in fluid communication with the second storage layer. The first storage layer has a first shape and the second storage layer has a second shape. The first shape is different from the second shape. Additionally, each of the first storage layer and second storage layer comprise less than about 20 percent airfelt.

The details of one or more embodiments of the invention are set forth in the accompanying drawings and the description below. Other features, objects and advantages of the invention will be apparent from the description and drawings, and from the claims.

BRIEF DESCRIPTION OF THE DRAWINGS

FIG. 21 is a top plan view of the incontinence pad of FIG. 1 in a folded configuration.

FIG. 22 is a section view along line 22-22 of FIG. 21.

FIG. 23 is a section view of an embodiment of a wrapping sheet at area 21 of FIG. 22.

FIG. 24 is a section view of another embodiment of a wrapping sheet.

FIGS. 26-31B illustrate a method and apparatus for testing peel strength.

DETAILED DESCRIPTION

As used herein, the term "absorbent article" refers to devices which absorb and contain body exudates (e.g., urine and excrement), and more specifically, refers to devices which are placed against or in proximity to the body of the wearer to absorb and contain the various exudates discharged from the body.

The terms "absorbent pad" and "incontinence pad" refer to an absorbent article generally sized and shaped to fit in the crotch region of a wearer and generally configured to be worn with an undergarment, such as underwear.

As used herein, the term "disposable" is used to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" refers to an element being located in a particular place or position.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "layer," as used herein, does not necessarily limit an element to a single strata of material in that a layer may actually include a carrier material and another material carried thereon, laminates or combinations of sheets or webs, e.g., of the same or of differing materials.

A "unitary" absorbent article refers to absorbent articles which are formed of separate parts united together to form a coordinated entity so that they do not require separate manipulative parts like a separate holder and liner.

The term "longitudinal" refers to a direction running generally parallel to the maximum linear dimension of an element. Directions within ±45 degrees of the longitudinal direction are considered to be "longitudinal."

The term "lateral" refers to a direction running generally at a right angle to the longitudinal direction. Directions within ±45 degrees of the lateral direction are considered to be "lateral."

For purposes of describing an embodiment of the invention, the description below will focus on adult incontinence pad examples. However, these embodiments are exemplary as aspects may apply to other absorbent articles, such as incontinence briefs, diapers, incontinence undergarments, absorbent inserts, absorbent liners, sanitary napkins, and the like.

U.S. Provisional Application Ser. No. 60/710,032 filed on Aug. 19, 2005 and U.S. Provisional Application Ser. No. 60/818,109 filed on Jun. 30, 2006, describe disposable absorbent articles which are constructed in accordance with the present invention.

A. Incontinence Pad

Figure 1:
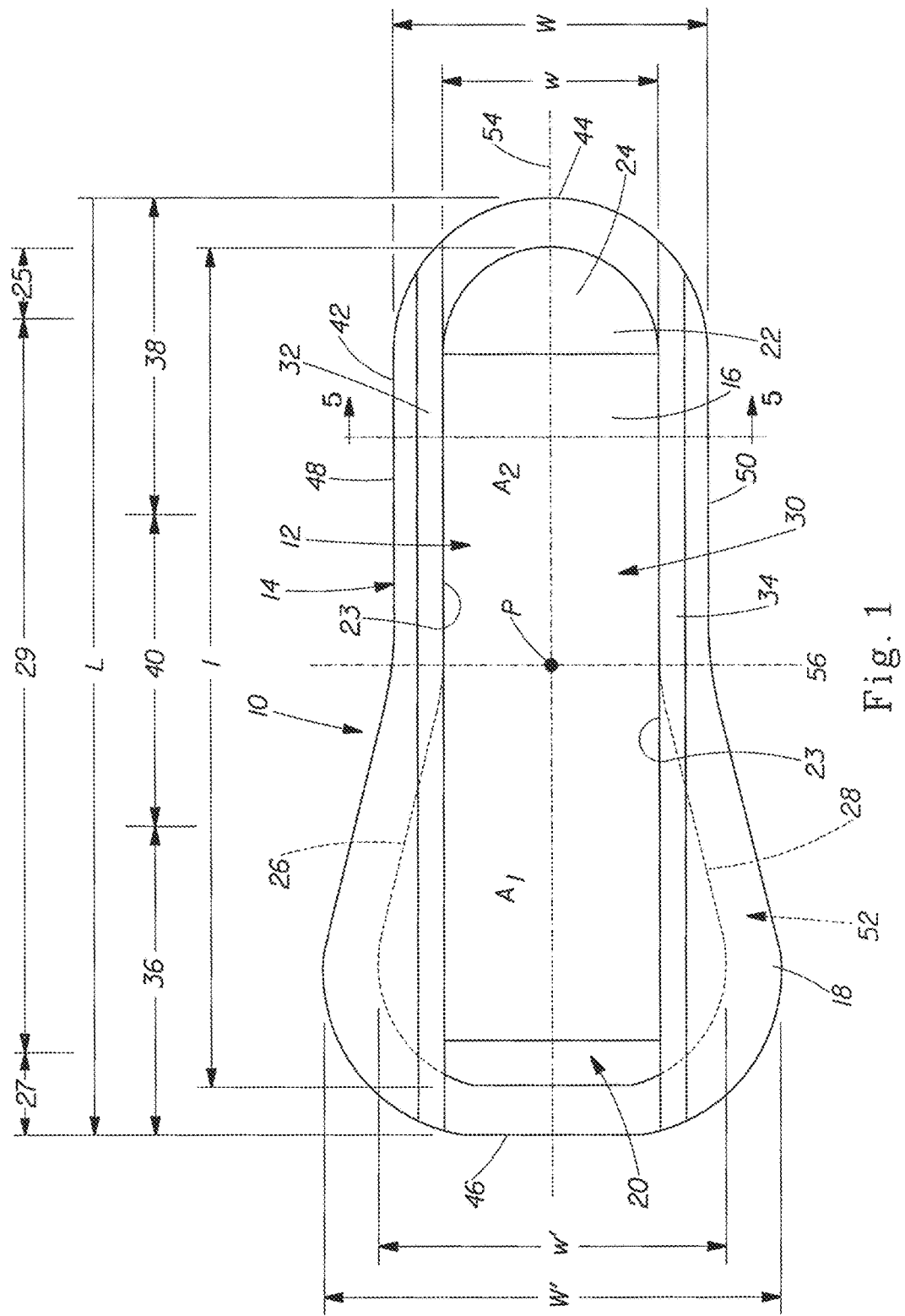
FIG. 1 is a top plan view of an embodiment of an incontinence pad with the body-facing surface of the pad facing the viewer.

Referring to FIG. 1, an adult incontinence pad 10 is shown in a flat, laid-out state with a body-facing portion 12 of the incontinence pad 10 oriented towards the viewer. The incontinence pad 10 may include a chassis 14 with a liquid permeable topsheet 16 and a liquid impermeable backsheet 18 joined to the topsheet 16 to form a core receiving volume 20 located therebetween. An absorbent core 22 can be disposed in the core receiving volume 20, between the topsheet 16 and the backsheet 18. As shown, in some embodiments, the absorbent core 22 may include a storage layer 24 having opposite side edges 26 and 28 (shown only in part by the dotted lines) and an acquisition system 30 located between the storage layer 24 and the topsheet 16.

Incontinence pad 10 may further include a first elasticized leg cuff 32 extending longitudinally along a length of the body-facing portion 12 and a second elasticized leg cuff 34 extending longitudinally along a length of the body-facing portion 12 aligned with (e.g., substantially parallel to) the elasticized leg cuff 32. As used herein, the term "longitudinal" refers to a direction substantially parallel to a longitudinal axis 54 of the incontinence pad 10.

Each elasticized leg cuff 32, 34 include a respective standing line 23. Standing lines 23 include a first portion 25 that is bonded to the topsheet 16 at a first end of the elasticized leg cuffs 32, 34, a second portion 27 that is bonded to the topsheet 16 at a second, opposite end of the leg cuffs 32, 34 and a free portion 29 unbonded to the topsheet 16 between the first and second portions 25 and 27. In some embodiments, standing lines 23 can be about 15 mm or less from a closest longitudinal edge of the acquisition system 30.

B. Incontinence Pad Shape and Sizing

Incontinence pad 10 is shown to have a back region 36, a front region 38 opposite the back region 36, a crotch region 40 between the back region 36 and the front region 38, and a periphery 42, which, in the illustrated example, is formed by an outer perimeter of backsheet 18 which includes end edges 44 and 46 and side edges 48 and 50. Back region 36 extends from end edge 44 to the crotch region 40 and front region 38 extends from end edge 46 to crotch region 40. The terms front and back regions are used merely to differentiate between pad regions and not to denote a preferred pad position during use.

Body-facing portion 12 includes that portion of the incontinence pad 10 which is positioned adjacent to a wearer's body during use. A garment-facing portion 52 of the incontinence pad 10 includes that portion of the incontinence pad 10 which is positioned adjacent a garment of the wearer during use. Garment-facing portion 52 is generally formed by at least a portion of the backsheet 18 and, in some embodiments, by other components joined to the backsheet 18.

Incontinence pad 10 has a pair of axes, the longitudinal axis 54 and a lateral axis 56 that extends substantially transverse to the longitudinal axis. Each axis 54, 56 passes through a point P located at the geometric center of the incontinence pad 10. In the illustrated embodiment, longitudinal axis 54 intersects each of the end edges 44 and 46 and spans a maximum length L of the incontinence pad 10, while lateral axis 56 intersects the side edges 48 and 50. In some embodiments, the longitudinal axis 54 may not span the maximum length of the incontinence pad 10. In certain instances, lateral axis 56 spans a minimum width W of the incontinence pad 10.

Periphery 42 of the incontinence pad 10 defines a pad shape. As shown by FIG. 1, the pad shape can be asymmetric about the lateral axis 56 in that the pad shape is not substantially identical on each side of the lateral axis 56. For example, as shown, in some embodiments, area $A_1$ of the incontinence pad 10 that includes back region 36 can be substantially greater than area $A_2$ that includes front region 38. In some embodiments, $A_1$ may be about five percent larger or more (e.g., about 10 percent larger, about 15 percent larger, about 20 percent larger, etc.) than $A_2$.

As shown, the pad shape of the incontinence pad 10 can be symmetric about the longitudinal axis 54 in that the pad shape is substantially identical on each side of the longitudinal axis 54. However, in some embodiments, the pad shape can be asymmetric about the longitudinal axis 54 in that the pad shape is not substantially identical on each side of the longitudinal axis 54. In some embodiments, the pad shape may be symmetric about the lateral axis 56 in that the pad shape is substantially identical on each side of the lateral axis 56.

Incontinence pad 10 can be sized and designed for improved wearer comfort while providing desired properties, such as capacity and acquisition properties. As will be described below, incontinence pad 10 can provide improved wearer comfort while providing desired properties, such as capacity (e.g., about 5 ml or greater, about 200 ml or greater) and acquisition properties (e.g., about 1.5 g of 0.9 percent NaCl solution per second or greater under a pressure of about 0.3 psi) through use of, in some embodiments, superabsorbent material (which can, for instance, comprise a particulate absorbent gel material or an AGM present in any shape, including particles, fibers, spheres, foamed sheets, flakes, rods, and the like) in the absorbent core 22, which can also allow a caliper (i.e., a measured thickness) of the incontinence pad 10 to be thin (e.g., about 20 mm or less).

In some embodiments, incontinence pad 10 can have a maximum length L (e.g., about 260 mm, about 284 mm, about 304 mm, about 324 mm), and/or a minimum width W (e.g., about 85 mm, about 100 mm) and/or a maximum width W' (e.g., about 130 mm, about 140 mm). Additionally, in some embodiments, the absorbent core 22 of the incontinence pad 10 can have a maximum length l (e.g., about 230 mm, about 254 mm, about 274 mm, about 294 mm), a minimum width w (e.g., about 50 mm, about 65 mm) and a maximum width w' (e.g., about 100 mm, about 110 mm). In some embodiments, L, W, W', l, w and w' can be selected to correspond to small, medium, large and fill figure body types. In many implementations, L, W, W', l, w and w' are selected to correspond to undergarment sizes, which can provide a guide for incontinence pad selection by a wearer.

Figure 2:
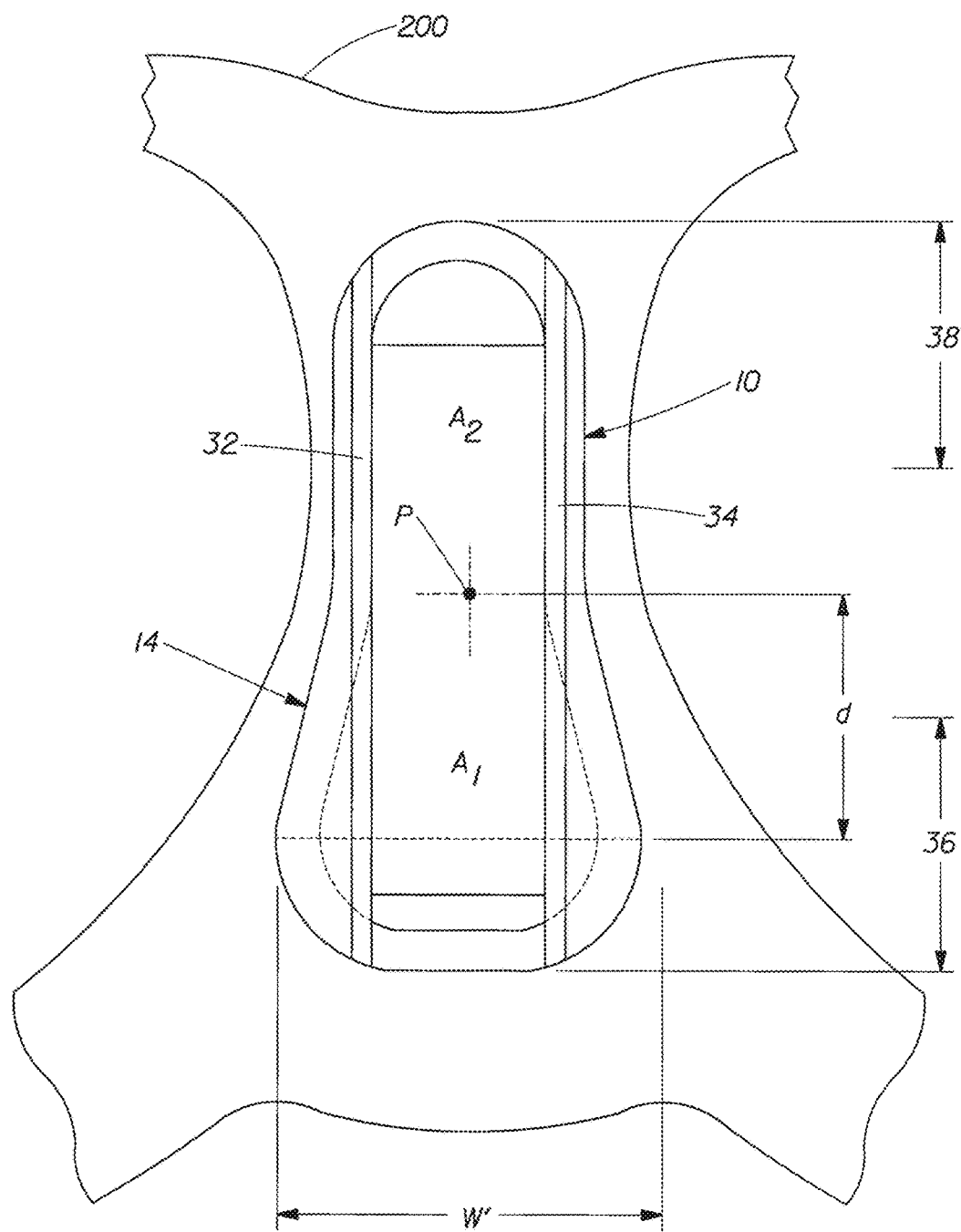
FIG. 2 is a top plan view of the incontinence pad of FIG. 1 affixed to an undergarment with the body-facing surface of the pad facing the viewer.

Referring now to FIG. 2, a diagrammatic illustration of an incontinence pad 10 affixed to a female undergarment 200 (i.e., a panty). As an illustrative example, the table below presents panty survey data for United States briefs. This survey data can be used to correlate the size of the incontinence pad 10 with undergarment 200 size.

TABLE I

U.S. Panty Measurement Data

|  | Brief |
|---|---|
| Minimum Crotch Width, mm |  |
| Average/St Dev | 69/9 |
| Range | 48–85 |
| Front** Crotch Width, mm |  |
| Average | 175/36 |
| Range | 127–250 |
| Back** Crotch Width, mm |  |
| Average | 188/47 |
| Range | 124–320 |

**Front and Back dimensions measured 90 mm from minimum crotch width

Along with the above survey data, other parameters may be considered in correlating pad size and undergarment size. For example, it may be desirable to size the incontinence pad 10 to fit entirely within the undergarment 200 so that no portion of the incontinence pad projects beyond the undergarment 200 during use. An example of such an incontinence pad 10 is shown in FIG. 2. This sizing can include both the width of the incontinence pad 10 and the length of the incontinence pad 10. In some instances, however, a portion of the incontinence pad 10 may project beyond the undergarment 200 during use. Additionally, it may be desirable to size the incontinence pad 10 so that the leg cuffs 32 and 34 may be positioned at opposite sides of the crotch to provide a leak barrier along each side between chassis 14 and the wearer's body.

The table below illustrates a correlation between panty sizes and incontinence pad sizes. It should be noted that various embodiments can include other size correlations.

TABLE II

Panty Size/Incontinence Pad Correlation Chart

| | Panty Size | | | |
|---|---|---|---|---|
| | ≤4/5/6 | ~7/8/9 | ~10/11/12 | 13+ |
| | Pad Size | | | |
| | Small | Medium | Large | X-Large |
| Pad Length (L) | 255 mm +/− 40 mm | 280 mm +/− 40 mm | 305 mm +/− 40 mm | 330 mm +/− 50 mm |
| Minimum Pad Width (W) | 80 mm +/− 20 mm | 85 mm +/− 20 mm | 90 mm +/− 20 mm | 95 mm +/− 30 mm |

TABLE II-continued

Panty Size/Incontinence Pad Correlation Chart

| | Panty Size | | | |
|---|---|---|---|---|
| | ≤4/5/6 | ~7/8/9 | ~10/11/12 | 13+ |
| | Pad Size | | | |
| | Small | Medium | Large | X-Large |
| Maximum Pad Width (W') | 120 mm +/− 20 mm | 130 mm +/− 20 mm | 140 mm +/− 20 mm | 150 mm +/− 30 mm |
| Minimum Core Width (w) | 60 mm +/− 20 mm | 65 mm +/− 20 mm | 70 mm +/− 20 mm | 75 mm +/− 30 mm |
| Maximum Core Width (w') | 100 mm +/− 20 mm | 110 mm +/− 20 mm | 120 mm +/− 20 mm | 130 mm +/− 30 mm |
| Pad caliper | 6 mm +/− 3 mm | 6 mm +/− 3 mm | 6 mm +/− 3 mm | 6 mm +/− 3 mm |
| Pad capacity | 250 g +/− 100 g | 250 g +/− 100 g | 250 g +/− 100 g | 250 g +/− 100 g |

While the above table includes four incontinence pad sizes, in some implementations, there may be less than (e.g., three pad sizes) or more than four pad sizes (e.g., five pad sizes). As one example, a small pad size may correspond to 4/5/6 panty sizes, a medium pad size may correspond to 7/8/9 panty sizes and a large pad size may correspond to 10 and up panty sizes. As another example, a small pad size may correspond to 3/4/5 panty sizes, a medium pad size may correspond to 6/7/8 panty sizes, a large pad size may correspond to 9/10 panty sizes and a full figure pad size may correspond to 11 and up panty sizes. Other implementations are contemplated.

Front portion 38 of the incontinence pad 10 can be sized to fit comfortably within a wearer's crotch, between the legs of the wearer. A location of the maximum pad width W' at the back portion 36 of the incontinence pad 10 can be offset a distance d (e.g., 90 mm) from center point P so that the maximum pad width W' can be located away from between a wearer's legs during use whether the back portion 36 and corresponding larger area $A_1$ is located at the front of the wearer's body (e.g., during the daytime, for example, when front leakage may be of greatest concern) or at the rear of the wearer's body (e.g., during the nighttime, for example, when rear leakage may be of greatest concern).

Figure 3:
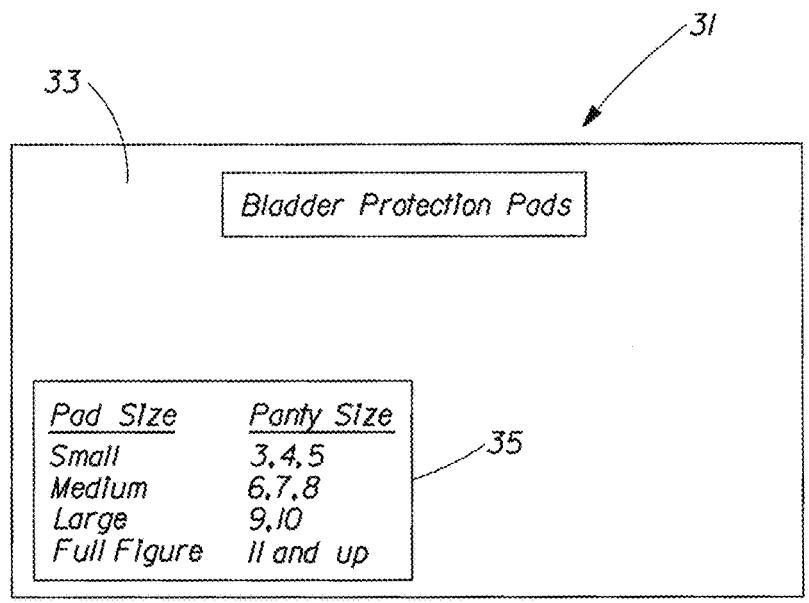
FIG. 3 is a diagrammatic illustration of an embodiment of an incontinence pad product.

The above-described sizing information can be used to generate indicia for a wearer to utilize in selecting an incontinence pad 10 size. Referring to FIG. 3, an incontinence pad product 31 includes a package 33 and multiple incontinence pads 10 (e.g., five pads, 10 pads, 15 pads, 20 pads, etc.) located therein. Incontinence pads 10 of the product 31 may all be the same size or may be of differing sizes, such as any of those described above. Visibly printed on the package 33 is indicia 35 for use in determining a desired incontinence pad size, e.g., for purchase and use. A wearer, upon determining a garment size, can refer to the indicia 35 to determine an incontinence pad size corresponding to the garment size. In some embodiments, the indicia may be printed separate from the package 33, for example, as part of a display (not shown). Other examples are possible.

Use of superabsorbent material in the core 22 allows for a relatively consistent pad caliper, capacity and/or acquisition properties regardless of pad size. In accordance with certain aspects of the invention, the core 22 is manufactured (e.g., has length and width properties) to fit a small pad size (see Table II). The core 22 can be stretched, if desired, when integrated into pads of larger sizes. It should be appreciated that stretching the core 22 may correspondingly reduce the pad thickness (or caliper). It should be further appreciated that the core 22 need not be stretched. Instead, because the core 22 provides suitable absorbency across the range of pad sizes, a core sized to fit a given pad can be attached as-is to larger pads.

Accordingly, in some embodiments, an incontinence pad 10 having a length L of about 255 mm (e.g., corresponding to a small size pad in Table II) may have pad caliper of no more than about 50 percent (e.g., no more than about 40 percent, about 35 percent, about 30 percent, about 25 percent, about 20 percent, about 15 percent, about 10 percent, about five percent, about three percent) greater than an incontinence pad 10 having a length L of about 330 mm (e.g., corresponding to an extra large pad size in Table II), while maintaining desired capacity and acquisition properties. In some embodiments, there may be relatively little deviation in pad caliper (e.g., no more than about 50 percent, about 40 percent, about 35 percent, about 30 percent, about 25 percent, about 20 percent, about 15 percent, about 10 percent, about five percent, about three percent) between any two, any three, any four, or even all incontinence pad 10 sizes between the smallest size available for purchase and the largest size available for purchase illustrated in Table II. Furthermore, the caliper of the pad 10 may have substantially no variation from one pad size to the next.

More broadly stated, as a pad size increases from a first size to a second size having a body-facing surface area between about 5% and about 40% greater than the body-facing surface area of the first size, the pad thickness (or caliper) decreases by an amount less than about 50 percent (e.g., less than about 40 percent, about 35 percent, about 30 percent, about 25 percent, about 20 percent, about 15 percent, about 10 percent, about five percent, about three percent). Furthermore, the caliper of the pad 10 may have substantially no variation (e.g., within one percent) from one pad size to the next.

By providing incontinence pads 10 having relatively consistent pad calipers amongst pad sizes while providing desirable capacity and acquisition properties for all the pad sizes, the pad sizing information (e.g., such as that shown by FIG. 3) can be relied upon more for wearer selection of a comfortable incontinence pad 10 rather than absorptive qualities of the pad. This can diminish the inducement for a wearer to select an under-absorptive incontinence pad for comfort or an uncomfortable, improperly sized pad for needed increased absorbency.

C. Incontinence Pad Components

Figure 4:
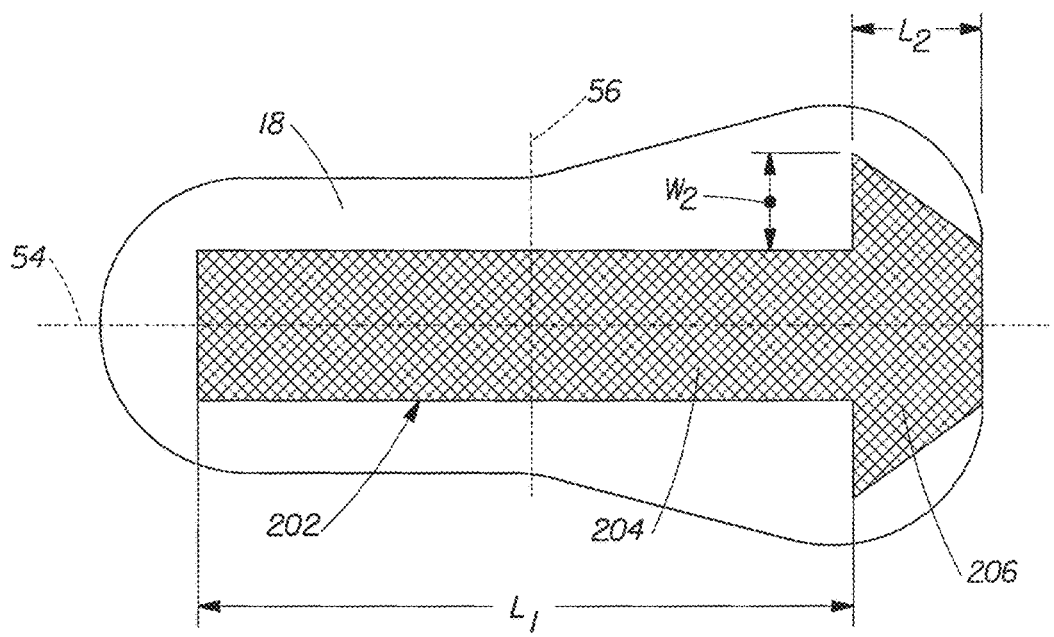
FIG. 4 is a back view of the incontinence pad of FIG. 1.

For use in affixing the incontinence pad 10 to the undergarment 200, incontinence pad 10 may include an adhesive region of adhesive material that is applied to backsheet 18 at the garment-facing portion 52 (shown in FIG. 1). Referring to FIG. 4, adhesive region 202 can be somewhat mushroom or T-shaped having a relatively narrow, elongated portion 204 and a wider, shorter portion 206. In some embodiments, adhesive region 202 has a length $L_1$ (e.g., about 201 mm), length $L_2$ (e.g., about 40 mm), width $W_1$ (e.g., about 40 mm) and width $W_2$ (e.g., about 30 mm). In some embodiments, the portion 206, being wider than portion 204, may be associated with the back portion 36 of the incontinence pad 10 having the maximum width W'. As shown, in some embodiments, the adhesive region 202 can be asymmetric about lateral axis 56 and symmetric about longitudinal axis 54. In other embodiments, shape of the adhesive region 202 may be symmetric about lateral axis 56 and/or asymmetric about longitudinal axis 54. Embodiments are contemplated where the adhesive region 202 is asymmetric about both the lateral axis 56 and the longitudinal axis 54. Additionally, embodiments are contemplated where the adhesive region 202 is symmetric about both the lateral axis 56 and the longitudinal axis 54. In some implementations, adhesive region 202 is applied to about 20 percent or more (e.g., about 30 percent or more, e.g., about 35 percent or more, such as about 37 percent) of the surface area of garment facing portion 52 of the backsheet 18.

Any suitable releasable adhesive material can be used to form the adhesive region 202, some examples of which include, NSC 2823 commercially available from National Starch and Chemical Co. and HL1461AZP commercially available from H.B. Fuller. In some embodiments, adhesive region 202 can provide a peel strength of between about 70 gf/40 mm and about 800 gf/40 mm or any individual number within the range. In some embodiments, the adhesive region can provide a peel strength of between about 200 gf/40 mm and about 800 gf/40 mm using the hereinafter described Peel Strength Test.

Figure 5A:
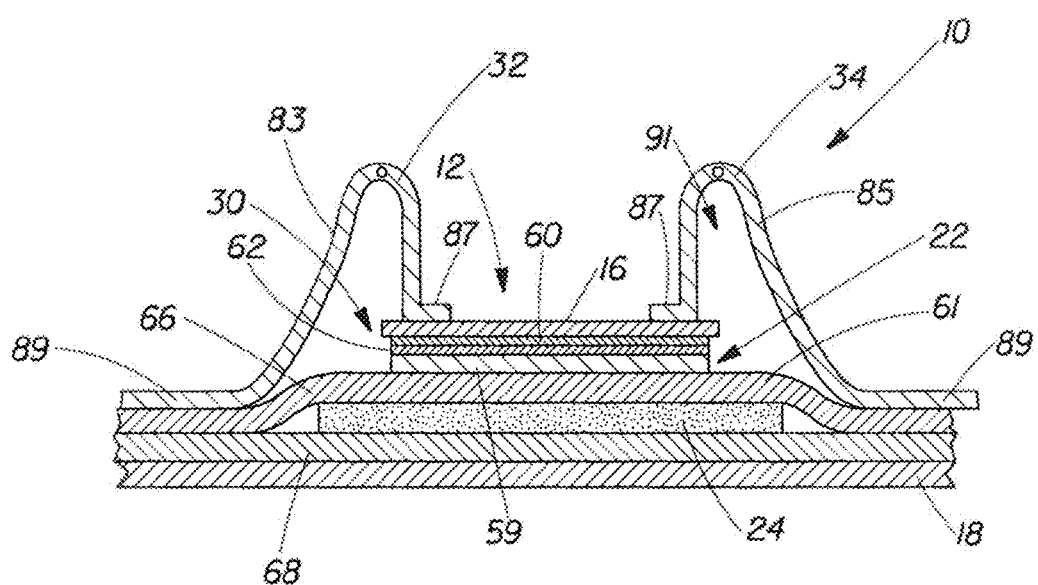
FIG. 5A is a section view of the incontinence pad of FIG. 1 taken along line 5A-5A of FIG. 1.

Referring to FIG. 5A, the absorbent core 22 is disposed between the topsheet 16 and the backsheet 18. Topsheet 16 may be fully or partially elasticized or may be foreshortened to provide a void space between the topsheet 16 and the absorbent core 22. Topsheet 16 can be formed of a compliant, soft-feeling and non-irritating material that is liquid pervious permitting liquids (e.g., urine) to readily penetrate through the thickness of the topsheet 16.

Any suitable topsheet may be utilized in the present invention. For example, in a specific embodiment, a nonwoven material for forming topsheet 16 is a carded nonwoven material of polypropylene, which is commercially available from Amoco Fabrics, under Code No. Doft P-10, 23 Stly 007. As another example, in some embodiments, the topsheet 16 may include an odor reduction layer. Such a topsheet 16 can be formed by a non-woven material which is treated with, for example, metalphthalocyanine material so that it can function as an odor reduction layer.

Backsheet 18 is generally positioned away from the wearer's skin and can inhibit exudates absorbed and contained in the absorbent core 22 from wetting articles which contact the incontinence pad 10 such as undergarments. The backsheet 18 can be impervious to liquids (e. g., urine) and can be manufactured from a laminate of a non-woven and a thin plastic film, although other flexible materials may be used. An example of a suitable material for the backsheet 18 is a thermoplastic film having a thickness of from about 0.012 mm (0.5 mil) to about 0.051 mm (2.0 mils). Other examples of suitable backsheet films include those manufactured by Tredegar Industries Inc. of Terre Haute, Ind. and sold under the trade names X15306, X10962, and X10964.

In some embodiments, suitable backsheet materials may include breathable materials that permit vapors to escape while still preventing exudates from passing through the backsheet 18. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097.

As shown in FIG. 5A, the absorbent core 22 generally is disposed between the topsheet 16 and the backsheet 18. Absorbent core 22 may include any absorbent material that is generally compressible, conformable, non-irritating to the wearer's skin, and capable of absorbing and retaining liquids such as urine and other certain body exudates. The absorbent core 22 may include a wide variety of liquid-absorbent materials commonly used in disposable diapers and other absorbent articles such as comminuted wood pulp, which is generally referred to as air felt. Examples of other suitable absorbent materials include creped cellulose wadding, melt blown polymers including co-form, chemically stiffened, modified or cross-linked cellulosic fibers, tissue including tissue wraps and tissue laminates, absorbent foams, absorbent sponges, superabsorbent polymers, absorbent gelling materials, or any other absorbent material or combinations of materials.

In some embodiments, the absorbent core 22 can be a substantially airfelt free core as described in U.S. patent application Ser. No. 10/776,851 (Becker et. al), published as U.S. Publication No. 2004/0162536. Further examples of suitable absorbent core constructions are described in U.S. Publication No. 2004/0167486 to Busam et al. The absorbent core of the aforementioned publication, in one embodiment, uses no or minimal amounts of absorbent fibrous material within the core. Generally, the absorbent core may include no more than about 20 weight percent of absorbent fibrous material (i.e., [weight of fibrous material/total weight of the absorbent core]×100).

In some embodiments, absorbent core 22 may include the acquisition system 30 which may comprise an upper acquisition layer 60 adjacent the topsheet 16, a middle acquisition layer 62 and a lower acquisition layer 59 above a storage layer 24. The upper acquisition layer 60, the middle acquisition layer 62, and the lower acquisition layer 59 can be in fluid communication with each other. In one embodiment, the upper acquisition layer 60 includes a non-woven and the middle acquisition layer 62 includes a mixture of chemically stiffened, twisted and curled fibers, high surface area fibers and thermoplastic binding fibers. In another embodiment, acquisition layers 60 and 62 are provided from a non-woven material, which is preferably hydrophilic and lower acquisition layer 59 is a mixed bonded air laid non-woven material. The lower acquisition layer 59 may or may not be in direct contact with the storage layer 24. In some embodiments, the middle acquisition layer 62 may include chemically stiffened, twisted and curled fibers without thermoplastic binding fibers. In some embodiments, lower acquisition layer 59 may include treated pulp fibers.

Storage layer 24 may be wrapped by a core wrap material 61. In the illustrated embodiment, the core wrap material 61 includes a top layer 66 and a bottom layer 68. The top layer 66 and the bottom layer 68 may be provided from two or more separate sheets of materials or they may be alternatively provided from a unitary sheet of material. Such a unitary sheet of material may be wrapped around the storage layer 24 in any suitable manner, e.g., in a C-fold.

The core wrap material 61, the top layer 66 and/or the bottom layer 68 can be provided from a non-woven material. One specific example of a non-woven material includes a spunbonded, a melt-blown and a further spunbonded layer, i.e., an SMS material. Permanently hydrophilic non-wovens, and in particular nonwovens with durably hydrophilic coatings can be used. In another example, the nonwoven material may include a spunbonded layer, two adjacent melt-blown layers and another spunbonded layer or SMMS structure.

Some examples of non-woven materials can be provided from synthetic fibers, such as polyethylene (PE), polyethylene terephthalate (PET) and polypropylene (PP). As polymers used for non-woven production may be inherently hydrophobic, they may be preferably coated with hydrophilic coatings. An example of a suitable method of producing non-wovens with durably hydrophilic coatings is via applying a hydrophilic monomer and a radical polymerization initiator onto the non-woven, and conducting a polymerization activated via ultraviolet (UV) light resulting in monomer chemically bound to the surface of the non-woven. Another example of a suitable method of producing a non-woven with durably hydrophilic coatings is to coat the non-woven with hydrophilic nanoparticles.

Typically, nanoparticles have a largest dimension of below 750 nm. Nanoparticles with sizes ranging form 2 to 750 nm can be economically produced. The advantages of nanoparticles is that many of them can be easily dispersed in water solution to enable coating application onto the non-woven; they typically form transparent coatings, and the coatings applied from water solutions are typically sufficiently durable to exposure to water.

Nanoparticles can be organic or inorganic, synthetic or natural. Inorganic nanoparticles generally exist as oxides, silicates, carbonates. Typical examples of suitable nanoparticles are layered clay minerals (e.g., LAPONITE from Southern Clay Products, Inc. (USA), and Boehmite alumina (e.g., DISPERAL P2 from North American Sasol Inc.) Other suitable examples of nanoparticles are described in U.S. Pat. No. 6,863,933 and U.S. Pat. No. 6,645,569.

In some cases, the non-woven surface can be pre-treated with high energy treatment (corona, plasma) prior to application of nanoparticle coatings. High energy pre-treatment typically temporarily increases the surface energy of a low surface energy surface (such as PP) and thus enables better wetting of a non-woven by the nanoparticle dispersion in water. This method is discussed in U.S. Pat. No. 6,863,933 and U.S. Pat. No. 6,645,569.

Figure 5B:
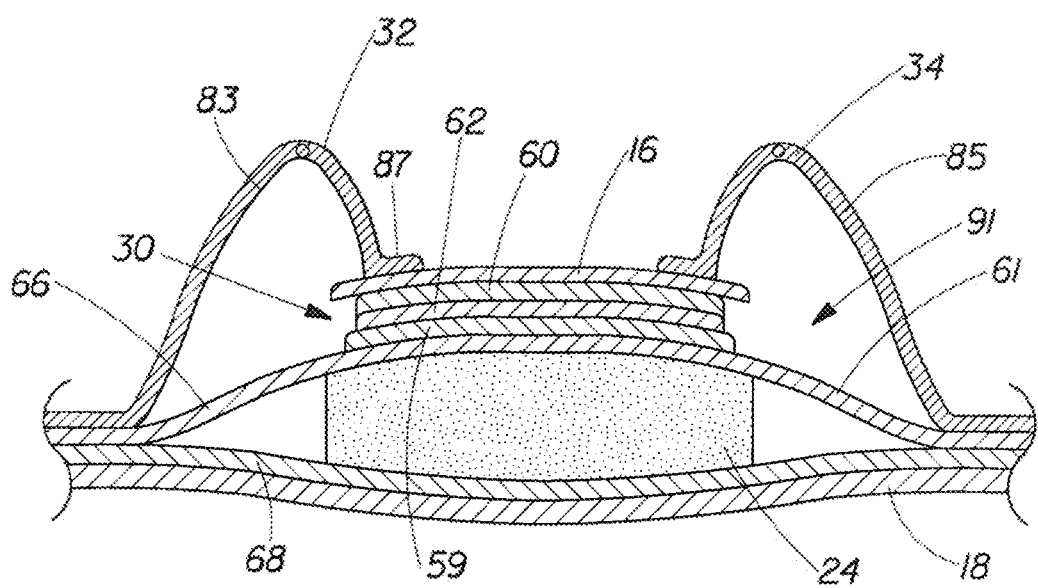
FIG. 5B is a section view of the incontinence pad similar to FIG. 5A but showing the pad in an expanded state.

As shown in FIG. 5A, in some embodiments, barrier leg cuff sheets 83 and 85 (e.g., formed of any suitable material such as a woven or non-woven material) can be affixed to the top sheet 16 and the core wrap 61 to form the barrier leg cuffs 32 and 34. A first longitudinal edge 87 of the respective barrier leg cuff sheets 83 and 85 can be affixed to the topsheet 16 and an opposite, second longitudinal edge 89 of the respective barrier leg cuff sheets 83 and 85 can be affixed to the top layer 66 of the core wrap 61 at a location spaced outward from the first longitudinal edge 87. As shown, the first and second longitudinal edges 87 and 89 can be bonded so as to provide an expandable volume 91 capable of expanding (or increasing) in response to expansion of the storage layer 24 (See FIG. 5B).

Figure 6A:
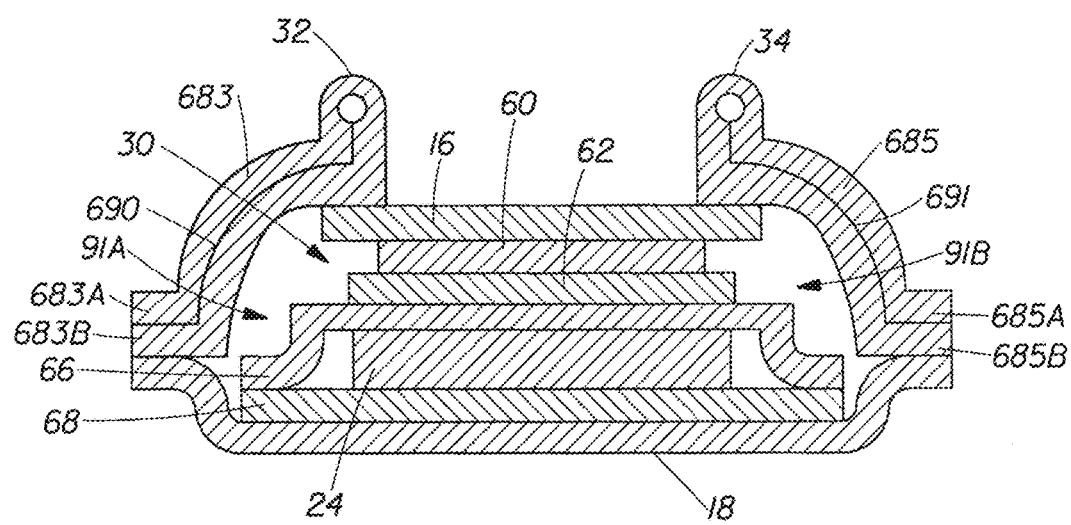
FIG. 6A is a section view of another embodiment of an incontinence pad constructed in accordance with the present invention.

As shown in FIG. 6A, a barrier leg cuff sheet 683 and a barrier leg cuff sheet 685 can be joined to the topsheet 16 and the backsheet 18. Embodiments are contemplated where the barrier leg cuff sheets 683 and 685 are joined to the topsheet 16 and/or the top layer 66 of the core wrap 61. The barrier leg cuff sheet 683 may comprise an unattached portion 690, and the leg cuff sheet 685 may comprise an unattached portion 691.

As shown, in some embodiments, the barrier leg cuff sheets 683 and/or 685 may comprise a single unitary web which is folded upon itself to form the first layer 683A and second layer 683B and/or the first layer 685A and the second layer 685B, respectively. In some embodiments, the barrier leg cuff sheets 683 and/or 685 may comprise separate webs which make up the first layer 683A and the second layer 683B and the first layer 685A and the second layer 685B, respectively.

One benefit of the dual layered barrier leg cuff sheets 683 and/or 685 is that the first layer can act as a backup to the second layer. For example, during processing of the non-woven, typically, because of the random assembly of fibers into a web, portions of the nonwoven can have poor uniformity. For example, in the case of a single layer with poor uniformity, there may be leakage in some areas due to the poor uniformity. In contrast, with a dual layered cuff sheet, as discussed above, the likelihood of poor uniformity in both layers at the same location is small. As such, the risk of leakage through a dual layered cuff sheet is minimized.

Figure 6B:
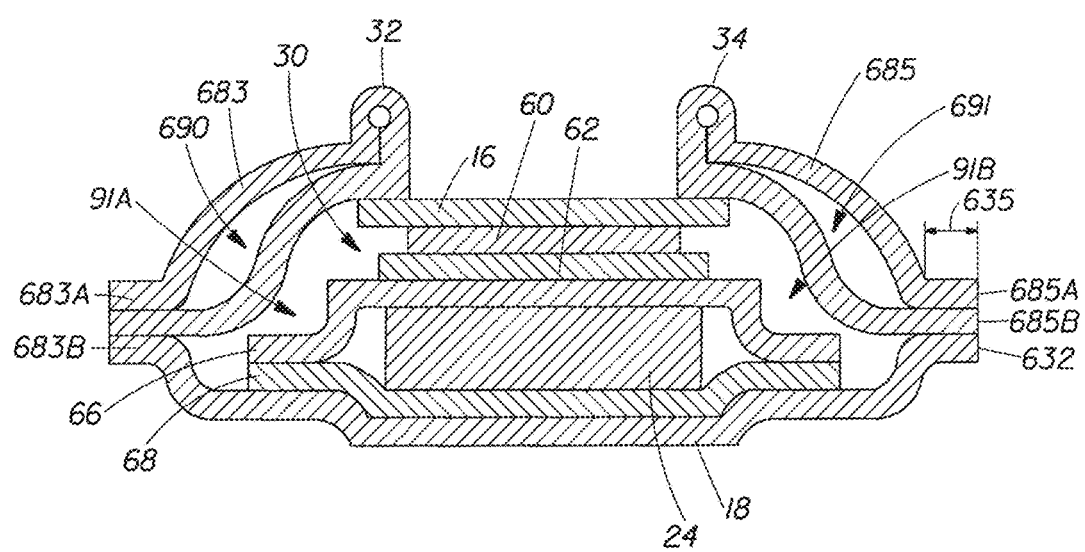
FIG. 6B is a section view showing the incontinence pad of FIG. 6A in an expanded state.

Another benefit of the dual layered barrier leg cuff sheets 683 and/or 685 pertains to the amount of glue proximate to the perimeter of the pad. For example, as shown in FIG. 6B, adhesive can be applied between the first layer 685A, second layer 685B, and/or the backsheet 18 proximate to the end edge 632. The adhesive can have a width 635 of about 7 mm. However, in some embodiments, the first layer 685A, the second layer 685B and/or the backsheet 18 can be crimped together proximate to the end edge 632. By crimping these elements together, the width of adhesive applied can be reduced or the adhesive applied between various elements can be reduced and/or eliminated. For example, when crimping is utilized, the width 635 of adhesive can be less than about 7 mm. As another example if the first layer 685A and the second layer 685 are crimped together, then adhesive may only need to be applied to join the backsheet 18 and the crimped barrier leg cuff material. As yet another example, when crimping is utilized, the adhesive about the perimeter, e.g., proximate to the end edge 632, can be eliminated. The reduced amount of adhesive applied about the perimeter of the pad can increase the softness of the pad thereby increasing the comfort of the wearer.

Figure 7:
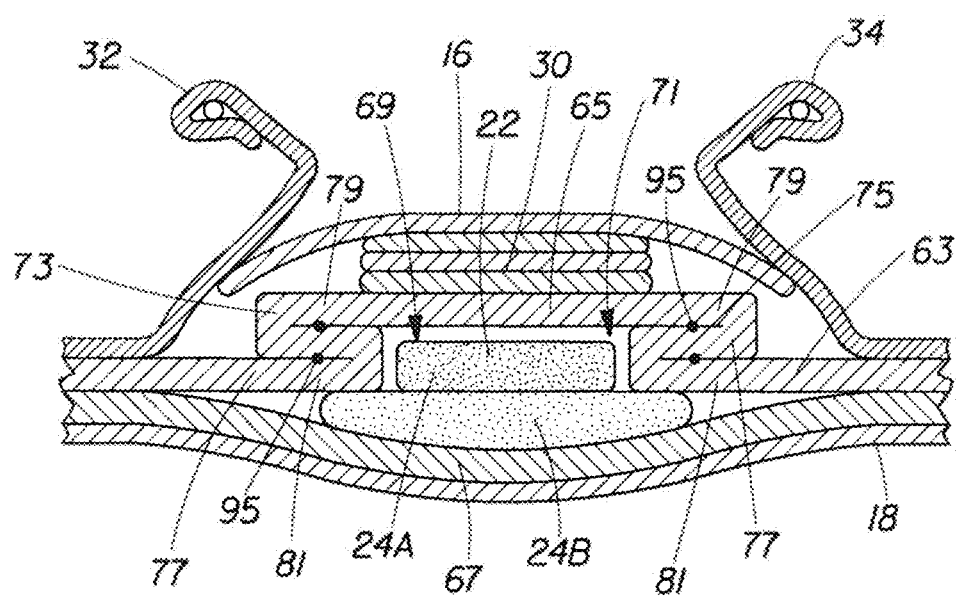
FIG. 7 is a section view of another embodiment of an incontinence pad.

Referring now to FIG. 7, in some embodiments, storage layer 24 (here formed of layers 24A and 24B) may be wrapped with a core wrap 63 including top layer 65 and bottom layer 67, for example, formed from a non-woven material such as those exemplified above with reference to layers 66 and 68. Top layer 65 can be joined to bottom layer 67 to define a core receiving volume 69 and an expandable volume 71. Expandable volume 71 (shown in a contracted state) is expandable, as needed, to accommodate expansion of the storage layer 24 as liquid is being stored therein. As shown, in some embodiments, the volume provided between the top and bottom layers 65 and 67 can be relatively small with the expandable volume 71 in the contracted state and can contain the storage layer 24 relatively tightly between the top layer 65 and the bottom layer 67. In some embodiments, a nonwoven layer and/or tissue layer can separate the layer 24A from the layer 24B.

The layers 24A and 24B of the storage layer 24 may comprise identical materials in some embodiments. For example, the layers 24A and 24B may each comprise an AGM and may each have a basis weight of about 320 gsm. Some suitable examples of AGM are available from Nippon Shokubai of Tokyo, Japan under the product codes of L600 and L595 and available from BASF under the product code of ASAP600z. Examples of other suitable materials include those described with regard to the absorbent core heretofore.

In contrast, in some embodiments, the layers 24A and/or 24B may comprise varying basis weights of AGM with respect to one another. For example, in some embodiments, the layer 24A may comprise a higher basis weight of AGM than the layer 24B. In other embodiments, the layer 24B may comprise a higher basis weight of AGM than the layer 24A.

Additionally, in some embodiments, the layer 24A may comprise a different form of AGM than the layer 24B. For example in some embodiments, the layer 24A may comprise particles having a spherical shape while the layer 24B comprises rod shaped particles. Furthermore, in some embodiments, the layer 24A may comprise a different particle size than the layer 24B. For example, layer 24A may comprise AGM particles having an average particle size of about 50 microns while layer 24B may comprise AGM particles having an average particle size of about 1000 microns. Particle size of AGM particles can be measured as discussed in U.S. Pat. No. 6,096,299.

Figure 9:
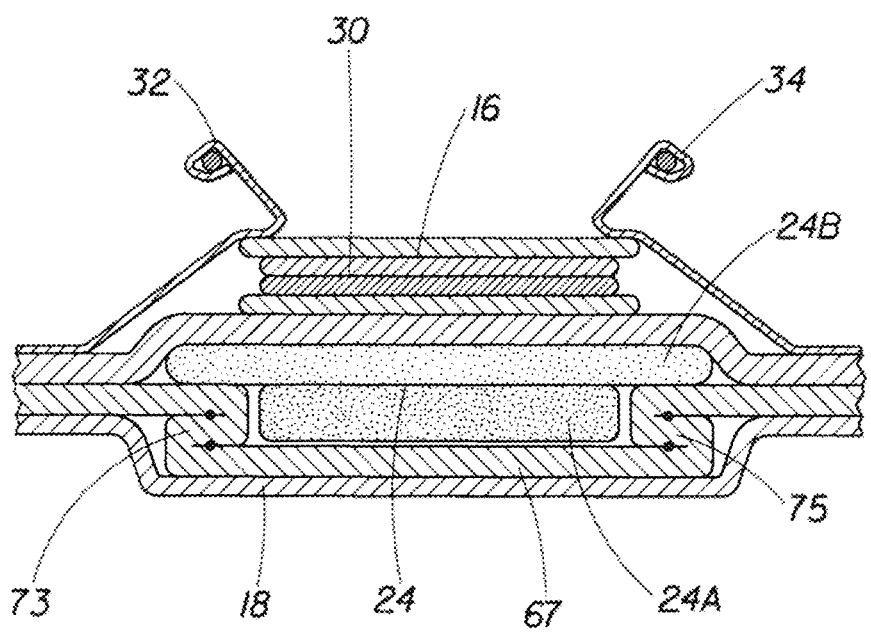
FIG. 9 is a section view of another embodiment of an incontinence pad.

As shown in FIG. 7, in some embodiments, the layer 24A may be disposed superajacent to the layer 24B. In contrast, as shown in FIG. 9, in some embodiments, the layer 24B can be disposed superadjacent to the layer 24A. In some embodiments, the layer 24A may have a substantially constant width (generally parallel to the lateral axis 56 (shown in FIG. 1). In contrast, in some embodiments, the layer 24B may be shaped and generally follow the curvature of the periphery 42 (shown in FIG. 1) of the incontinence pad 10 (shown in FIG. 1). Embodiments are contemplated where the shape of the storage layer 24A is different from the shape of the storage layer 24B. For example, the first storage layer may be substantially rectangular while the second storage layer may form a portion of the outer periphery of the incontinence pad 10. As another example, the storage layer 24A may have a first width in the second region, and the storage layer 24B can have a second width in the second region. In some embodiments, the first width can be less than the second width or vice versa.

Additionally, in some embodiments, the layer 24A may comprise more surface area than the layer 24B. In contrast, in some embodiments, the layer 24A may comprise a smaller surface area than the layer 24B. Alternatively, in some embodiments, the layer 24A may comprise about the same surface area as the layer 24B.

Additionally, embodiments are contemplated where the layer 24A and the layer 24B are profiled. For example, the layer 24A may comprise a higher gsm of AGM in the front region 38 (shown in FIG. 1) as opposed to the back region 36 (shown in FIG. 1) or vice versa. As another example, the layer 24A may comprise a higher gsm in the crotch region 40 (shown in FIG. 1) than both the front region 38 (shown in FIG. 1) and the back region 36 (shown in FIG. 1). As yet another example, the layer 24A may comprise a higher gsm of AGM on one side of the longitudinal axis 54 than the other side. As yet another example, the layer 24A may comprise a higher gsm of AGM on one side of the lateral axis 56 than on the other side of the lateral axis 56. Any suitable combination of the examples presented above can be combined to form a profiled layer 24A. Additionally, embodiments are contemplated where the layer 24A and/or the layer 24B are configured as described above.

As shown in FIG. 7, expandable volume 71 may be provided through use of a first fold structure 73 and a second fold structure 75 formed in the top layer 65 of the core wrap 63, in some embodiments. The first fold structure 73 and the second fold structure 75 may extend longitudinally along a length of the incontinence pad 10 generally parallel to one another. The first and second fold structures 73 and 75 can be spaced-apart from each other to allow for the expandable volume 71 to be provided therebetween.

In the unexpanded state, in some embodiments, the folds 77 of each fold structure 73, 75 can be located between and adjacent to an upper portion 79 and a lower portion 81 of the top layer 65. As shown, in some embodiments, the first and second fold structures 73 and 75 can be located between the storage layer 24 and the acquisition system 30. Additionally, the acquisition system 30 can be located between the topsheet 16 and the top layer 65 of the core wrap 63.

Bonds 95 may be formed (e.g., through use of adhesive) between folds 77 of the fold structures 73 and 75 to provide resistance to unintended expansion and unfolding of the fold structures 73, 75. In some embodiments, other adhesive materials or fasteners may be used to provide resistance such as adhesive tape. Some examples of adhesives suitable for use in the fold structures 73 and 75 include product codes NW1151, HL1358LO, and D3155B, each available from H.B. Fuller Co. of St. Paul, Minn.; and product codes 519 and 526, each available from National Starch Co. of Bridgewater, N.J.

Figure 8:
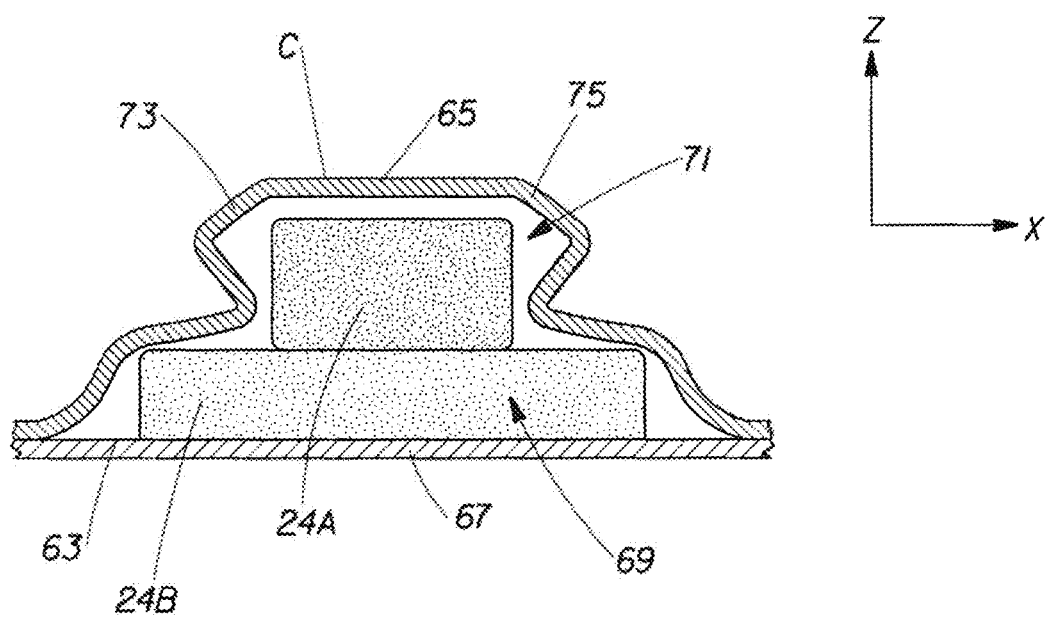
FIG. 8 is a section view of the incontinence pad of FIG. 7 in an expanded state.

FIG. 8 shows expandable volume 71 in an expanded state, for example, due to forced expansion by the storage layers 24A and 24B, with the outer layers removed for clarity. As can be seen, the first and second fold structures 73 and 75 allow for expansion of the expandable volume 71 in the z direction, which increases the overall volume between the top layer 65 and the bottom layer 67 of the core wrap 63.

The fold structures 73 and 75 can be sized such that the expandable volume 71 can accommodate substantially full expansion of the storage layer 24 with the storage layer 24 at its full fluid carrying capacity. In some embodiments, expandable volume 71 increases a total volume formed between the top layer 65 and bottom layer 67 by about 10 percent or more. For example, the expandable volume 71 can increase the total volume by about 15 percent, by about 20 percent, by about 25 percent, by about 30 percent, by about 35 percent, by about 40 percent, by about 45 percent, or by about 50 percent or more. Additionally, in certain implementations, the expandable volume 71, when expanded, can increase non-woven circumference C about the periphery of the core wrap 63 by about 10 percent or more. For example, the expandable volume 71, when expanded, can increase the circumference C about the periphery of the core wrap 63 by about 15 percent, by about 20 percent, by about 25 percent, by about 30 percent, by about 35 percent, by about 40 percent, by about 45 percent, or by about 50 percent or more.

Figure 10:
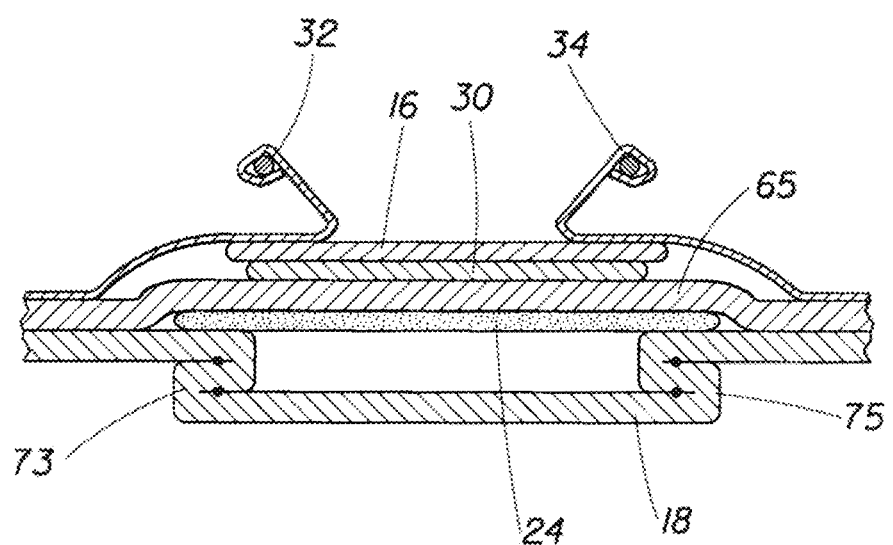
FIG. 10 is a section view of another embodiment of an incontinence pad.

Referring to FIG. 9, in some embodiments, fold structures 73 and 75 can be formed in bottom layer 67 in a fashion similar to that described above. As shown in FIG. 10, in some embodiments, fold structures 73 and 75 may be formed in more outer layers, such as backsheet 18. In some embodiments (not shown), fold structures 73 and 75 may be formed in more than one layer, such as in top layer 65 and in bottom layer 67. For example, a fold structure may be formed in a top layer 65 while a fold structure 75 is formed in a bottom layer 67, or vice versa. As another example, the fold structure 73 and/or fold structure 75 may each comprise a portion of both the top layer 65 and a portion of the bottom layer 67.

Figure 11A:
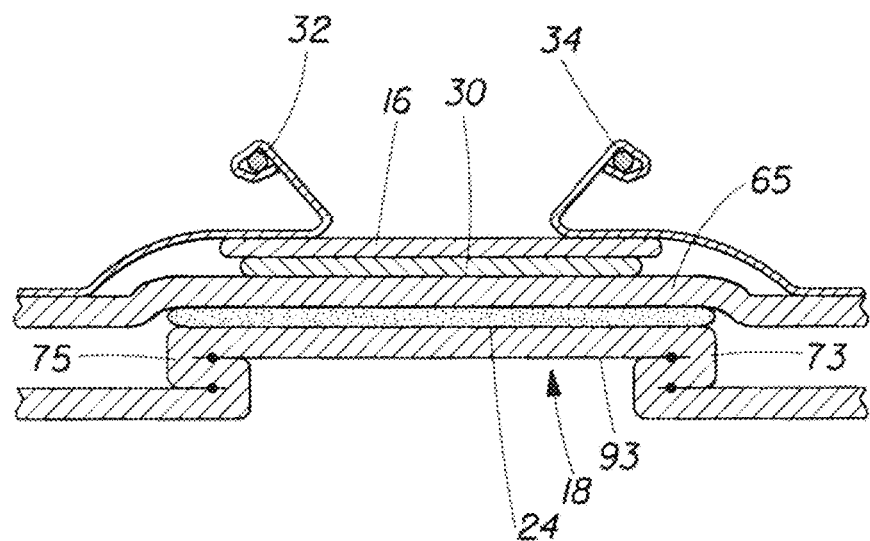
FIG. 11A is a section view of another embodiment of an incontinence pad.

Referring to FIG. 11A, still other embodiments of the present invention contemplate that the backsheet 18 can be configured opposite to that illustrated in FIG. 10. For instance, a raised middle portion 93 can extend between the opposing fold structures 73 and 75. Accordingly, during operation, when the storage layer 24 expands, the raised middle portion 93 can be biased downwards while the fold structures 73 and 75 unfold to accommodate the swelling. It should be appreciated that the fold configuration of FIG. 11A can alternatively be achieved by the top layer 65 and the bottom layer 67, if desired.

Figure 11B:
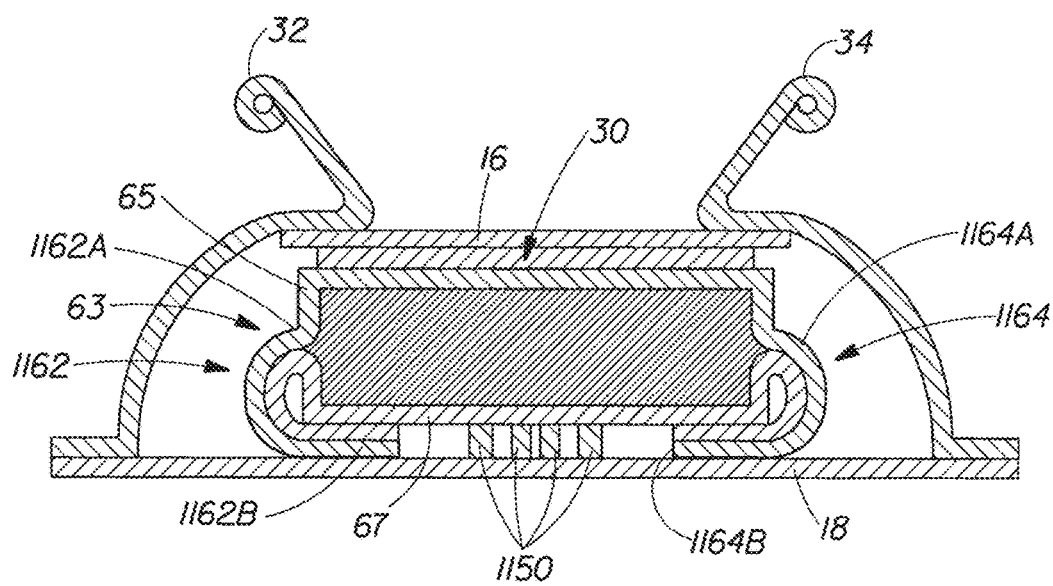
FIG. 11B is a section view of another embodiment of an incontinence pad.

As stated previously and as shown in FIG. 11B, the core wrap 63 may comprise the top layer 65 and the bottom layer 67 in some embodiments. As shown, in some embodiments, the top layer 65 and the bottom layer 67 can be joined to one another outboard of the storage layer 24, thereby forming fold structures 1162 and 1164. The core wrap 63 can be joined to the backsheet 18 via adhesive elements 1150. The adhesive elements 1150 can join the core wrap 63 and storage layer 24 to the backsheet 18 in the relative center of the article.

As shown, the fold structure 1162 may comprise a proximal area 1162A and a distal area 1162B. Similarly, the fold structure 1164 may comprise a proximal area 1164A and a distal area 1164B. As shown, the distal areas 1162B and 1164B can be folded under the bottom layer 67. In this embodiment, the distal areas 1162B and 1164B can be unbonded to either the backsheet 18 or the bottom layer 17, thereby allowing the distal areas 1162B and 1164B to move relative to the core wrap 63.

Upon being wetted, the storage layer 24 expands. Upon expansion of the storage layer 24, the top layer 65 and the bottom layer 67 can separate from each other adjacent to the proximal areas 1162A and 1162B of the fold structures 1162 and 1164, respectively. The separation of the top layer 65 from the bottom layer 67 adjacent to the proximal areas 1162A and 1164A can accommodate the expansion of the storage layer 24. Additionally, because the distal areas 1162B and 1164B can be unbonded to the either the backsheet 18 or the bottom layer 67, the distal areas 1162B and 1164B can be displaced from between the backsheet 18 and the bottom layer 67 upon expansion of the storage layer 24.

The top layer 65 and the bottom layer 67 can be joined by any suitable manner known in the art. An example of a suitable means is the adhesive utilized for the bonds 95 discussed heretofore.

While Z-type and C-type fold structures are shown in FIGS. 7-11B, any other suitable fold structure can be employed such as multiple, bellow-type folds, ripples, etc., for example, having more than two folds each. Additionally, similar fold structures 73 and 75 may be formed in any of the topsheet 16, backsheet 18, at the leg cuffs 32, 34, as examples, to form a respective expandable portion that can expand, for example, in response to expansion of the absorbent core 22. Fold structures can reduce the tension in the wrap material and reduce the propensity for tearing the wrap material. As an alternative or in addition to fold structures materials may be formed of a stretchy or expansive material to allow for core expansion.

Additionally, while the barrier leg cuffs 32 and 34 of FIGS. 7-11B illustrate embodiments where the barrier leg cuff sheet includes a single layer, embodiments are contemplated where the barrier leg cuff sheet material comprises multiple layers as described with regard to FIGS. 6A and 6B.

Figure 12A:
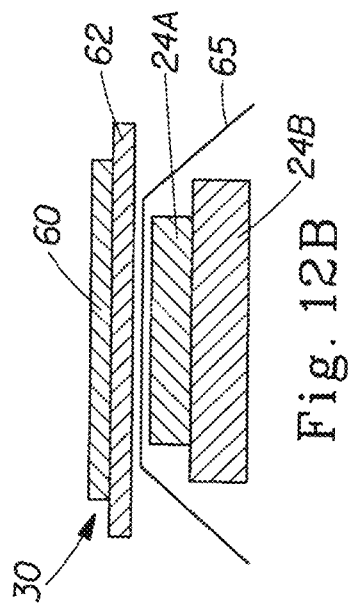
FIG. 12A is a section view of another embodiment of an incontinence pad.
Figure 12B:
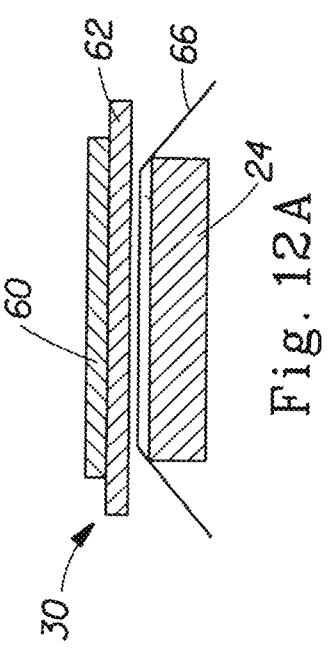
FIG. 12B is a section view of another embodiment of an incontinence pad.
Figure 12C:
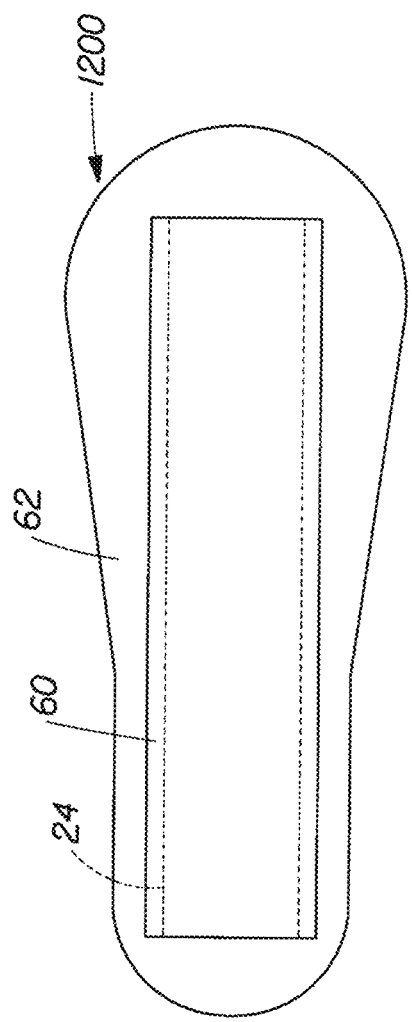
FIG. 12C is a plan view of the incontinence pad of FIG. 12A.

As stated previously, with regard to FIG. 5A, in some embodiments, the absorbent core 22 may comprise an acquisition system 30 which includes a plurality of layers and the storage layer 24. As shown in FIG. 12A, the acquisition system 30, in some embodiments, may comprise the upper acquisition layer 60 and the middle acquisition layer 62. As shown in FIG. 12B, the acquisition system 30 may be configured as described above. Additionally, the storage layer 24 may comprise multiple layers 24A and 24B.

In contrast to the incontinence pad 10 shown in FIG. 1, in some embodiments, the incontinence pad 1200 may comprise a substantially rectangular storage layer 24 and a substantially rectangular upper acquisition layer 60. As discussed previously, the size of the incontinence pad can vary greatly with panty size. However, by manufacturing the middle acquisition layer 62 to the desired size/shape based on the size of the panty, uniform sized storage layers 24 and uniform sized upper acquisition layers 60 may be utilized regardless of the size of the incontinence pad. By utilizing uniform sized storage layers 24 and uniform upper acquisition layers 60 across all sizes of panties, manufacturing complexity and cost reductions may be achieved.

The storage layers and/or the acquisition layers described herein may include any suitable shape known in the art. For example, the shape of an acquisition layer can be different from the shape of the storage layer. As another example, the shape of an acquisition layer can be asymmetric about the lateral and/or longitudinal axis of the incontinence pad 1200. As yet another example, the shape of a storage layer can be asymmetric about the lateral and/or longitudinal axis. As yet another example, an acquisition layer can have a first width in the first region and a second width in the second region. The first width can be less than the second width, or vice versa. As yet another example, a first acquisition layer can have a first acquisition shape, and a second acquisition layer can have a second acquisition shape. The first acquisition shape can be different from the second acquisition shape.

Embodiments are contemplated where the upper acquisition layer 60 and/or the middle acquisition layer 62 are manufactured to a desired shape based on the size of the panty and wherein the storage layer 24 is a uniform size throughout the varying sizes of panties. Additionally, embodiments, are contemplated where the storage layer 24 is manufactured in accordance with the shape of the overall article and wherein the upper acquisition layer 60 and/or the middle acquisition layer 62 are uniformly sized across all panty sizes. Additionally, embodiments are contemplated where the upper acquisition layer 60 and the middle acquisition layer 62 are the same size.

Additionally, embodiments are contemplated where the surface area of the acquisition layers vary with respect to each other and/or with respect to the surface area of the storage layer 24. For example, the surface area of an acquisition layer can be at least 50% greater than the surface area of the storage layer. As another example, the surface area of a first acquisition layer and/or a second acquisition layer can be at least as much as a surface area of the storage layer.

Figure 13:
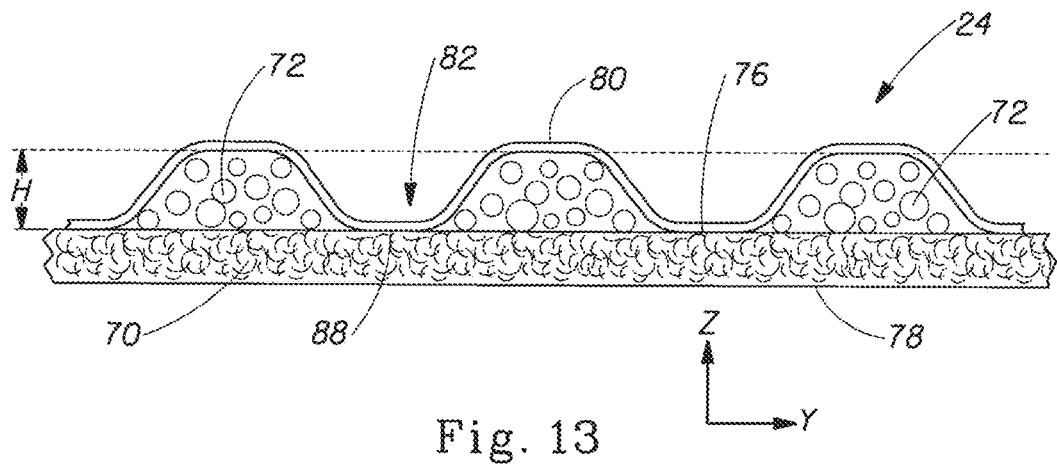
FIG. 13 is a section view of an embodiment of a storage layer.

Similarly to the storage layer 24 may be constructed in a number of different configurations. For example, as shown in FIG. 13, the storage layer 24 may include a substrate layer 70, absorbent polymer material 72 and a fibrous layer of adhesive 80. The substrate layer 70 can be provided from a non-woven material, for example, those exemplified above for the layers 66, 68. The absorbent polymer material 72 may be immobilized when wet such that the absorbent core 22, in some embodiments, achieves a wet immobilization of more than 50 percent, preferably of more than 60 percent, 70 percent, 80 percent or 90 percent according to the Wet Immobilization Test described herein.

The substrate layer 70 has a first surface 76 and a second surface 78. At least portions of the first surface 76 of the substrate layer 70 are in direct contact with a layer of absorbent polymer material 72.

The layer of absorbent polymer material 72 may be a discontinuous layer. As used herein, a discontinuous layer is a layer comprising areas where there is an absence of absorbent polymer material. In some embodiments, these areas can have a diameter or largest span of about 10 mm or less, about 5 mm or less, about 3 mm or less, about 2 mm or less, and of about 0.5 mm or more, at least about 1 mm or at least about 1.5 mm. The absorbent polymer material 72 defines a certain height H of the layer of absorbent polymer material 72 above the first surface 76 of the layer of substrate material 70. When the absorbent polymer material 72 layer is provided as a discontinuous layer, portions of the first surface of the substrate layer 70 may not be covered by absorbent polymer material 72. In some embodiments, the absorbent core 22 further comprises an adhesive 80 in the form of thermoplastic composition. This thermoplastic composition 80 can serve to at least partially immobilize the absorbent polymer material 72.

The height H of the layer of absorbent polymer material 72 can be any suitable height. In some embodiments, the height H can be lower than about 5 mm. In some embodiments, the height H can be about 2.5 mm or lower.

In one embodiment, the thermoplastic composition 80 can be disposed essentially uniformly within the polymeric absorbent material 72. However, in some embodiments the thermoplastic composition 80 can be provided as a fibrous layer which is partially in contact with the absorbent polymer material 72 and partially in contact with the substrate layer 70. As shown in FIG. 13, the absorbent polymer material 72 is provided as a discontinuous layer, the layer of fibrous thermoplastic composition 80 is laid down onto the layer of absorbent polymeric material 72, such that the thermoplastic composition 80 is in direct contact with the first surface of the layer of absorbent polymer material 72, but also in direct contact with the first surface 76 of the substrate layer 70 where the substrate layer 70 is not covered by the absorbent polymeric material 72. This imparts an essentially three-dimensional structure to the fibrous layer of thermoplastic composition 80 which, in itself, is essentially a two-dimensional structure of relatively small measured thickness.

The thermoplastic composition 80 can provide cavities 82 to hold the absorbent polymer material 72, and thereby immobilizes this material 72. In a further aspect, the thermoplastic composition 80 bonds to the substrate layer 70 and thus can affix the absorbent polymer material 72 to the substrate 70. In some implementations, thermoplastic composition 80 may also penetrate into both the absorbent polymer material 72 and the substrate layer 70, thus providing for further immobilization and affixation. While the thermoplastic materials disclosed herein provide a much improved wet immobilization (i.e., immobilization of absorbent material when the article is wet or at least partially loaded), these thermoplastic materials also provide a very good immobilization of absorbent material when the article is dry.

In some embodiments, the absorbent polymer material 72 may also be mixed with absorbent fibrous material, such as comminuted wood pulp generally referred to as airfelt material, which can provide a matrix for further immobilization of the super-absorbent polymer material. However, a relatively low amount of fibrous cellulose material may be used, for example, less than about 40 weight percent, less than about 20 weight percent or less than about 10 weight percent of cellulose fibrous material as compared to the weight of absorbent polymer material 72. Substantially airfelt free cores can be desired having about five weight percent or less airfelt material, such as no airfelt material. As used herein, the term "absorbent fibrous material" is not meant to refer to any thermoplastic material even if such thermoplastic material is fiberized and partially absorbent.

Figure 14:
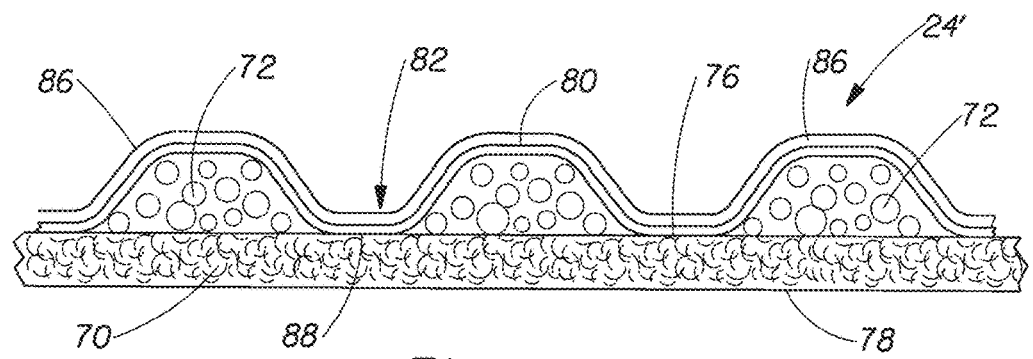
FIG. 14 is a section view of another embodiment of a storage layer.

An alternative storage layer embodiment is shown in FIG. 14. The storage layer 24' shown further comprises a cover layer 86. This cover layer 86 may be provided of the same material as the substrate layer 70, or may be provided from a different material. Preferred materials for the cover layer 86 are non-woven materials, typically the materials described above as useful for the layers 66 and 68. In this embodiment, portions of the cover layer 86 may bond to portions of the substrate layer 70 via the thermoplastic composition 80. Thereby, the substrate layer 70 together with the cover layer 86 can provide cavities to immobilize the absorbent polymer material 72.

Figure 15A:
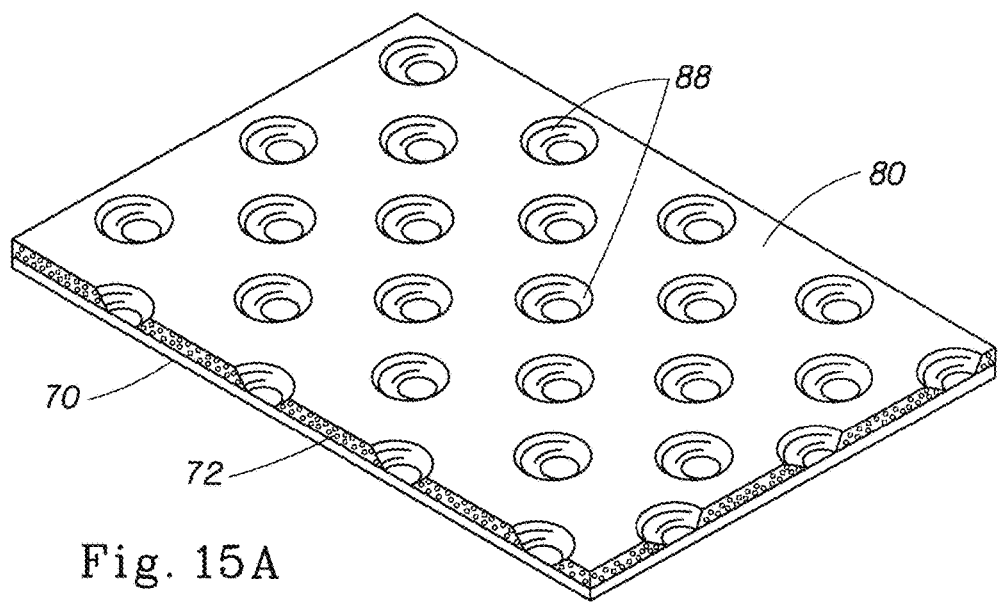
FIG. 15A is a perspective view of the storage layer of FIG. 13.

With reference to FIGS. 13 and 14 the areas of direct contact between the thermoplastic composition layer 80 and the substrate material 72 are referred to as areas of junction 88. The shape number and disposition of the areas of junction 88 will influence the immobilization of the absorbent polymer material 72. As shown in FIG. 15A, the areas of junction 88 may comprise a circular shape, in some embodiments. However, the areas of junction 88 can be any suitable shape known in the art, suitable examples of which include squared shape, rectangular shape, circular shape, triangular shape, polygonal shape, or any combination thereof. In embodiments where the areas of junction 88 comprise circular shapes, the circular shapes can have a diameter of more than about 0.5 mm, more than about 1 mm, more than about 1.5 mm and of less than about 10 mm, less than about 5 mm, less than about 3 mm, or less than about 2 mm. If the areas of junction 88 are not of circular shape, they may be of a size as to fit inside a circle of any of the preferred diameters given above.

Figure 15B:
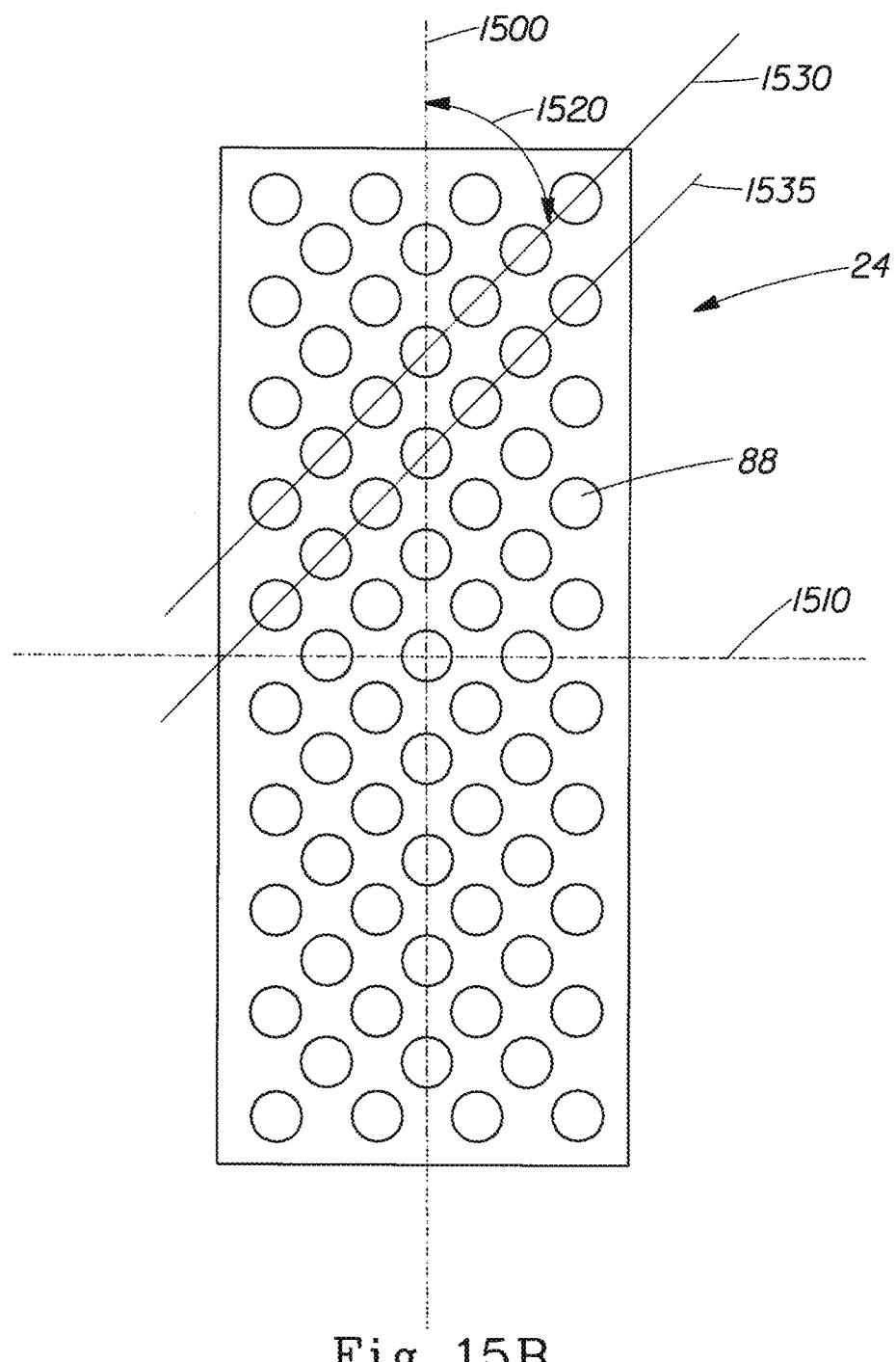
FIG. 15B is a plan view of the storage layer of FIG. 15A.

The areas of junction 88 can be disposed in a regular or irregular pattern. For example, as shown in FIG. 15B, in some embodiments, the areas of junction 88 may be disposed along lines 1530 and 1535. In some embodiments, the lines 1530 and 1535 may be aligned with a longitudinal axis 1500 of the storage layer 24, or alternatively they may have a certain angle 1520 in respect to longitudinal edges 108, 110 of the storage layer 24.

The lines 1530 and 1535 can be found by drawing a line through adjacent geometric centers of the areas of junction. For the purposes of illustration, columns of areas of junction 88 run generally parallel to the longitudinal axis 1500 of the storage layer 24. Pick a reference area of junction 88A. Pick the most adjacent areas of junction 88B and 88C. As shown, the areas of junction 88B and 88C can be in the columns adjacent to the column of the reference area of junction 88A. Note that in embodiments where lines 1530 and 1535 are aligned with the longitudinal axis 1500, the most adjacent areas of junction 88 to the reference area of junction 88A are in the same column as the reference area of junction 88A.

Draw line 1530 from the geometric center of the reference area of junction 88A to through the geometric centers of the adjacent areas of junction 88B and 88C. Extend the line 1530 to the longitudinal edges 108 and 110 of the storage layer 24. For areas of junction disposed between the areas of junction 88B and the longitudinal edge 110 and the area of junction 88C and the longitudinal edge 108, the line 1530 should be adjusted so that on average, the line 1530 cross through the geometric centers of as many areas of junction along the line 1530 as possible.

It has been found, that a disposition along lines parallel with the longitudinal edges 108, 110 of the storage layer 24 can create channels in the longitudinal direction which lead to a lesser wet immobilization. Therefore the areas of junction 88 are arranged along lines 1530 and/or 1535 which may form the angle 1520 of about 20 degrees, about 30 degrees, about 40 degrees, or about 45 degrees with a longitudinal axis 1500 of the storage layer 24. In some embodiments, the angle 1520 between the lines 1530 and 1535 of junctions 88 and the longitudinal axis 1500 of the storage layer 24 can be between about 10 degrees to about 45 degrees or any individual number within the range. In some embodiments, the angle 1520 between the line 1530 and the longitudinal axis 1500 can be greater than an angle between the line 1535 and the longitudinal axis 1500 of the storage layer 24. In some embodiments, the angle 1520 between the line 1530 and the longitudinal axis 1500 can be less than an angle between the line 1535 and the longitudinal axis 1500 of the storage layer 24.

Another preferred pattern for the areas of junction 88 is a pattern comprising polygons, for example pentagons and hexagons or a combination of pentagons and hexagons. Also preferred are irregular patterns of areas of junction 88, which also have been found to give a good wet immobilization.

Some fundamentally different patterns of areas of junctions 88 can be chosen in accordance with the present invention. For example, in one embodiment the areas of junctions 88 can be discrete and can be positioned within the areas of absorbent material 72, like islands in a sea. The areas of absorbent materials 72 are then referred to as connected areas. In an alternative embodiment, the areas of junctions 88 can be connected. Then, the absorbent material 72 can be deposited in a discrete pattern, or in other words the absorbent material 72 represents islands in a sea of thermoplastic material 80. Hence, a discontinuous layer of absorbent polymer material 72 may comprise connected areas of absorbent polymer material 72 or may comprise discrete areas of absorbent polymer material 72. In some embodiments, it has been found that absorbent cores providing for a good wet immobilization can be formed by combining two layers as shown in FIG. 13 and as described in the context thereof.

The thermoplastic layer 80 can be formed of any suitable thermoplastic composition, such as adhesive thermoplastic compositions, also referred to as hot melt adhesives. A variety of thermoplastic compositions are suitable to immobilize absorbent material.

Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behavior are herein also understood as suitable for forming thermoplastic composition 80.

Without wishing to be bound by theory it is believed that those thermoplastic compositions which may be useful for immobilizing the absorbent polymer material 72 are those that combine sufficient cohesion and adhesion behavior. Sufficient adhesion can ensure that the thermoplastic composition layer 80 maintains contact with the absorbent polymer material 72 and in particular with the substrate 70. Sufficient adhesiveness can be a challenge to achieve, namely when a non-woven substrate 70 is used. Sufficient cohesion can ensure that the adhesive does not rupture, in particular in response to external forces, and namely in response to strain. The adhesive is subject to external forces when the absorbent product has acquired liquid, which is then stored in the absorbent polymer material 72 which in response swells. An exemplary adhesive can allow for such swelling, without breaking and without imparting too many compressive forces, which would restrain the absorbent polymer material 72 from swelling. Additionally, the adhesive should not rupture, which may deteriorate the wet immobilization. In some instances, thermoplastic compositions meeting these requirements have the following features:

The thermoplastic composition may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

In some embodiments, the thermoplastic polymer can have a molecular weight (Mw) of more than 10,000 and a glass transition temperature (Tg) usually below room temperature. Typical concentrations of the polymer in a hot melt are in the range of about 20 to about 40 percent by weight or any individual number within the range. A wide variety of thermoplastic polymers are suitable. Such thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other examples of suitable thermoplastic polymers that may be employed are metallocene polyolefins, which are ethylene polymers prepared using single-site or metallocene catalysts. Therein, at least one co-monomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

In some embodiments, the thermoplastic resin can have a Mw below 5,000 and a Tg usually above room temperature, typical concentrations of the resin in a hot melt can be in the range of about 30 to about 60 percent or any individual number within the range. Additionally, in some embodiments, the plasticizer can have a low Mw of typically less than 1,000 and a Tg below room temperature, with a typical concentration of from about 0 to about 15 percent.

In some embodiments, the adhesive is present in the forms of fibers throughout the core. For example, the fibers can have an average thickness of from about 1 to about 50 micrometer or any individual number within the range. Additionally, the fibers can have an average length of about 5 mm to about 50 cm or any individual number within the range. To improve the adhesion of the thermoplastic composition 80 material to the substrate layer 70 or to any other layer, in particular any other non-woven layer, such layers may be pre-treated with an auxiliary adhesive. For example, in some implementations, the adhesive will meet at least one, and more preferably several or all of the parameters discussed below.

The adhesive can have a storage modulus G' measured at 20° C. of at least about 30,000 Pa and less than about 300,000 Pa or any individual number within the range. In some embodiments, the adhesive can have a storage modulus G' measured at 20 degrees C. of preferably less than about 200,000 Pa or more preferably less than about 100,000 Pa. The storage modulus G' at 20° C. is a measure for the permanent "tackiness" or permanent adhesion of the thermoplastic material used. Sufficient adhesion will ensure a good and permanent contact between the thermoplastic composition 80 material and for example the substrate layer 70.

In a further aspect, the storage modulus G' measured at 60° C. should be more than about 18,000 Pa and less than about 300,000 Pa or any individual number within the range. In some embodiments, the storage modulus G' measured at 60 degrees C. can be more than about 24,000 Pa or more preferably more than about 30,000. The storage modulus measured at 60° C. is a measure for the form stability of the thermoplastic composition 80 material at elevated ambient temperatures. This value is particularly important if the absorbent pad 10 is used in a hot climate where the thermoplastic composition 80 material would lose its integrity if the storage modulus G' at 60° C. is not sufficiently high.

Figure 16:
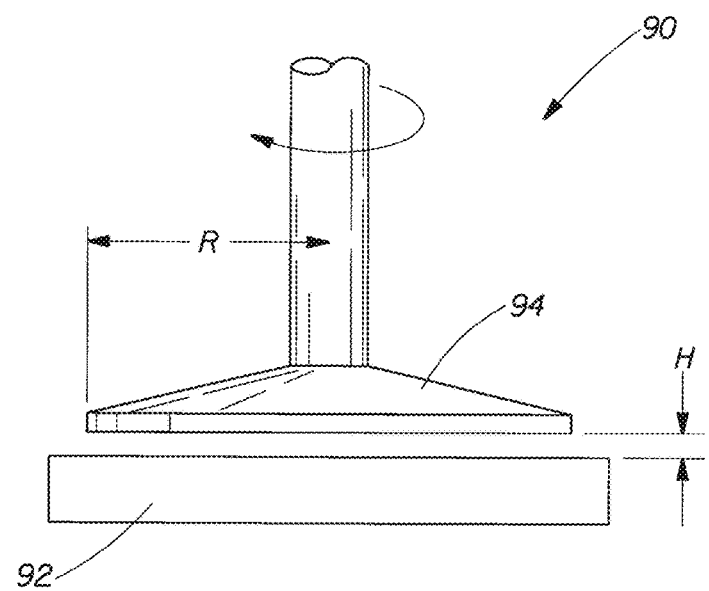
FIG. 16 is a diagrammatic view of an embodiment of a testing apparatus.

G' is typically measured using a rheometer 90 as schematically shown in FIG. 16 for the purpose of general illustration only. The rheometer 90 is capable of applying a shear stress to the adhesive and measuring the resulting strain (shear deformation) response at constant temperature. The adhesive is placed between a Peltier-element acting as lower, fixed plate 92 and an upper plate 94 with a radius R of, e.g., 10 mm, which is connected to the drive shaft of a motor to generate the shear stress. The gap between both plates has a height H of, e.g., 1500 micron. The Peltier-element enables to control the temperature of the material (+0.5° C.).

In a further aspect, the loss angle tan delta of the adhesive at 60° C. can be below the value of about 1, preferably below the value of about 0.5, in some embodiments. The loss angle tan delta at 60° C. is correlated with the liquid character of an adhesive at elevated ambient temperatures. The lower tan delta, the more an adhesive behaves like a solid rather than a liquid, i.e., the lower its tendency to flow or to migrate and the lower the tendency of an adhesive superstructure as described herein to deteriorate or even to collapse over time. This value may be particularly important if the absorbent pad 10 is used in a hot climate.

In a further aspect, the adhesive can have a glass transition temperature Tg of less than about 25° C., e.g., less than about 22° C., less than about 18° C., and less than about 15° C. A low glass transition temperature Tg is beneficial for good adhesion. In some instances, a low glass transition temperature Tg ensures that the adhesive thermoplastic material does not become too brittle.

In yet a further aspect, an adhesive can have a sufficiently high cross-over temperature Tx. A sufficiently high cross-over temperature Tx has, in some cases, been found beneficial for high temperature stability of the thermoplastic layer and can ensure performance of the absorbent pad 10 and in particular good wet immobilization even under conditions of hot climates and high temperatures. In some embodiments, Tx is above about 80° C., such as above about 85° C., such as above about 90° C.

In some embodiments, an adhesive material useful as a thermoplastic material 80 as described herein will meet most or all of the above parameters. Specific care must be taken to ensure that the adhesive provides good cohesion and good adhesion at the same time.

The process for producing preferred absorbent cores 22 may include a number of steps. For example, the absorbent core 22 can be laid down onto a laydown drum, which presents an uneven surface. In a first process step the substrate layer 70 can be laid on to the uneven surface. Due to gravity, or preferably by using a vacuum, the substrate layer material can follow the contours of the uneven surface and thereby the substrate layer material can assume peaks and valleys. Onto this substrate layer 70 absorbent polymeric material 72 is disposed by methods known in the art. The absorbent polymer material 72 will accumulate in the valleys presented by the substrate layer 70. In some embodiments, in a further process step a hot melt adhesive can placed onto the absorbent polymer material 72.

Any adhesive application means known in the art can be used to place the hot melt adhesive on to the absorbent polymer material 72. For example, the hot melt adhesive can be applied by a nozzle system. A nozzle system can provide a relatively thin but wide curtain of adhesive. This curtain of adhesive can then be placed onto the substrate layer 70 and the absorbent polymer material 72. As the peaks of the substrate layer 70 are less covered by absorbent polymer material 72 the adhesive can make contact with these areas of the substrate layer 70.

In an optional further process step a cover layer 86 can be placed upon the substrate layer 70, the absorbent polymer material 72 and the hot melt adhesive layer. The cover layer 86 will be in adhesive contact with the substrate layer 70 in the areas of junction 88. In these areas of junction 88, the adhesive is in direct contact with the substrate layer 70. The cover layer 86 will typically not be in adhesive contact with the substrate layer 70 where the valleys of the substrate layer 70 are filled with absorbent polymer material 72.

Alternatively the cover layer 86 can be laid down onto a drum with an uneven surface and the substrate layer 70 can be added in a consecutive process step. The embodiment shown in FIG. 13 can be produced by such a process.

In one alternative embodiment, the cover layer 86 and the substrate layer 70 can be provided from a unitary sheet of material. The placing of the cover layer 86 onto the substrate layer 70 will then involve the folding of the unitary piece of material.

Hence, the uneven surface of the lay-down system, which, for example, can be a lay-down drum, typically determines the distribution of absorbent polymeric material 72 throughout the storage layer 24 and likewise determines the pattern of areas of junction 88. Alternatively, the distribution of absorbent polymeric material 72 may be influenced by a vacuum.

The absorbent core can be formed utilizing storage layer 24, such as those described above. In some instances, no further materials wrapping the absorbent core 22, such as the top layer 66 and the bottom layer 68 are used. With reference to the embodiment of FIG. 13, in one embodiment, the substrate layer 70 may provide the function of the bottom layer 68 and the layer of fibrous thermoplastic material 80 (or cover layer 86 of FIG. 14) may provide the function of the top layer 66. With reference to FIG. 14 the cover layer 86 may provide the function of the top layer 66 and the substrate layer 70 may provide the function of the bottom layer 68.

In some embodiments, the distribution of absorbent polymeric material 72 varies along the storage layer 24, for example, in the longitudinal direction. Hence, along the longitudinal axis of the absorbent core 22, which is normally coincident with the longitudinal axis 54 of the incontinence pad 10, the basis weight of the absorbent polymer material 72 can change. In other embodiments, distribution of absorbent polymeric material may not be profiled and may be substantially constant along the longitudinal axis of the absorbent core 22.

In some embodiments having a varying distribution of absorbent polymer material 72, the basis weight of absorbent polymer material 72 in at least one freely selected first square measuring 1 cm$^2$ is at least about 10 percent, or about 20 percent, or about 30 percent, or about 40 percent, or about 50 percent higher than the basis weight of absorbent polymer material in at least one freely selected second square measuring 1 cm$^2$.

Optionally, the absorbent core 22 can also comprise an absorbent fibrous material, for example cellulose fibers. This fibrous material can be pre-mixed with the absorbent polymeric material 72 and be laid down in one process step or it can alternatively be laid-down in separate process steps.

It has been found beneficial to use a particulate absorbent polymer material 72 for absorbent cores 22. Without wishing to be bound by theory it is believed that such material, even in the swollen state, i.e., when liquid has been absorbed, does not substantially obstruct the liquid flow throughout the material, especially when the permeability as expressed by the saline flow conductivity of the absorbent polymer material 72 is greater than about 10, greater than about 20, greater than about 30, or greater than about 40 SFC-units, where 1 SFC unit is $1 \times 10^{-7}$ (cm$^3$s)/g.

As to achieve a sufficient absorbent capacity (e.g., at least about 1 g/cm$^2$ or more of 0.9 percent NaCl solution, at least about 2 g/cm$^2$ or more of 0.9 percent NaCl solution, such as between 2 g/cm$^2$ and 4 g/cm$^2$ of 0.9 percent NaCl solution, such as about 2.5 g/cm$^2$ of 0.9 percent NaCl solution) in an incontinence pad 10, superabsorbent polymer material 72 will be present with an average basis weight of about 50 g/m$^2$ or more. In some embodiments, density of absorbent material of the storage layer 24 may be about 400 g/m$^2$, such as about 500 g/m$^2$, such as about 600 g/m$^2$, such as about 700 g/m$^2$, such as about 800 g/m$^2$, such as about 900 g/m$^2$.

In some embodiments, a storage layer 24 formed of regions of absorbent polymer material 72 as described above may have a relatively small dry caliper. In some embodiments, storage layer 24 may have a dry caliper of about 5 mm or less, such as about 4 mm or less, such as about 2 mm or less and acquisition system 30 may have a dry caliper of about 4 mm or less and form about 50 percent or more of the total dry caliper of the incontinence pad 10. In some embodiments, the storage layer 24 may expand to a caliper of about 5 times or more than its dry caliper as the storage layer 24 absorbs liquid. In some instances, the storage layer 24 may swell to a caliper of about 2 cm or more at full capacity, such as between about 2 cm and about 6 cm, such as about 2.5 cm or any individual number within the range. In some embodiments, storage layer 24 may have a dry caliper that is about 50 percent or less (e.g., about 40 percent or less, about 30 percent or less, about 25 percent or less, about 20 percent or less, about 15 percent or less, about 10 percent or less, about 5 percent or less, and the like) of the total dry caliper of the absorbent core 22 and/or incontinence pad 10. In some embodiments, at full capacity, the storage layer 24 may swell to a wet caliper that is about 60 percent or greater (e.g., about 65 percent or greater, about 70 percent or greater, about 75 percent or greater, about 80 percent or greater, about 85 percent or greater, about 90 percent or greater) of the total caliper of the absorbent core 22 and/or incontinence pad 10.

D. Absorbent Core Shape and Sizing

Figure 17:
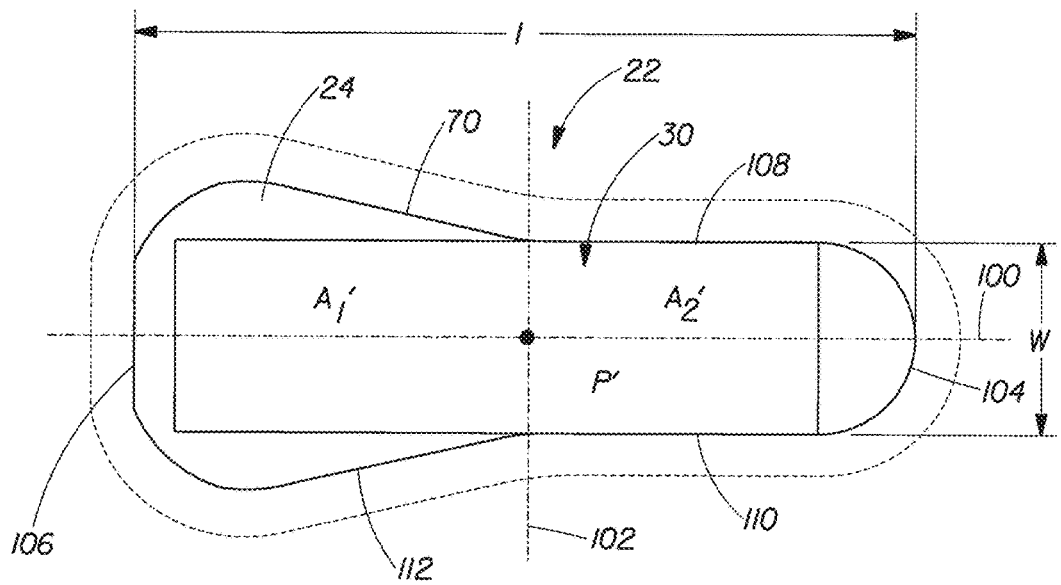
FIG. 17 is a top plan view of an absorbent core of the incontinence pad of FIG. 1.

Referring now to FIG. 17, a preferred absorbent core 22 configuration including storage layer 24 and acquisition system 30 is shown. Absorbent core 22 may extend along a pair of axes, e.g., a longitudinal axis 100 and a lateral axis 102 that extends substantially transverse to the longitudinal axis. Each axis 100, 102 extends through a point P' located at geometric center of the absorbent core 22. In the illustrated embodiment, longitudinal axis 100 intersects each of end edges 104 and 106 and spans a maximum length l of the absorbent core 22, while lateral axis 102 intersects side edges 108 and 110. In some embodiments, the longitudinal axis 100 may not span the maximum length of the storage layer 22. In certain instances, lateral axis 102 spans a minimum width w of the absorbent core 22 (FIG. 1).

Periphery 112 of the storage layer 24 can define a core shape. The periphery 112 may be formed by edges (e.g., edges 104, 106, 108, 110) of the substrate 70 of the storage layer 24 or, in some cases, by a core wrap (e.g., core wrap 61, 63). As shown by FIG. 17, the core shape, in some embodiments, can be asymmetric about the lateral axis 102 in that the core shape is not substantially identical on each side of the lateral axis 102. For example, area $A_1'$ of the storage layer 24 can be substantially greater than area $A_2'$. In some embodiments, $A_1'$ may be about five percent larger or more (e.g., about 10 percent larger, about 15 percent larger, about 20 percent larger, etc.) than $A_2'$. The core shape of the storage layer 24 can be symmetric about the longitudinal axis 100 in that the core shape is substantially identical on each side of the longitudinal axis 100. In an alternative embodiment, the core shape may be symmetric about the lateral axis 102 in that the core shape is substantially identical on each side of the lateral axis 102. In some implementations, the core shape is asymmetric about the longitudinal axis 100 in that the core shape is not substantially identical on each side of the longitudinal axis 100.

In some embodiments, the core shape of the absorbent core 22 (including any or all of components, such as the storage layer 24, forming the absorbent core) is a substantially similar shape to the pad shape (represented by dotted lines) of the incontinence pad 10. As used herein, similar shapes refer to figures having substantially the same shape and a different size.

Use of superabsorbent material in the core 22 allows for a relatively consistent core caliper, capacity and/or acquisition properties regardless of core size. As a result, in accordance with certain aspects of the invention, cores manufactured (e.g., having length and width properties) to fit a small pad size (see Table II) can be stretched, if desired, to be integrated into pads of larger sizes. It should be appreciated that stretching the core 22 may correspondingly reduce the core thickness (or caliper). Advantageously, certain aspects of the present invention have eliminated the need to separately manufacture various cores having sizes and shapes configured for specific pad sizes. It should be further appreciated that the core 22 need not be stretched. Instead, because the core 22 provides suitable absorbency across the range of pad sizes, a core sized to fit a given pad can be attached as-is to larger pads so long as the core is properly positioned for use.

As illustrated in Table II above, the core 22 can have a caliper that remains substantially constant across the range of pad sizes. The caliper can be anywhere at or between 3 mm, 4 mm, 5 mm, 6 mm, 7 mm, 8 mm, and 9 mm. In some embodiments, the core 22 (or storage layer 24) having l of about 230 mm (e.g., corresponding to a small pad size) may have a caliper of no more than about 50 percent (e.g., no more than about 40 percent, about 35 percent, about 30 percent, about 25 percent, about 20 percent, about 15 percent, about 10 percent, about five percent, and about three percent) greater than a core 22 (or storage layer 24) having an l of about 294 mm (e.g., corresponding to an extra large pad size), while maintaining desired capacity and acquisition properties. In some embodiments, there may be relatively little deviation in core or storage layer caliper (e.g., no more than about 50 percent, about 40 percent, about 35 percent, about 30 percent, about 25 percent, about 20 percent, about 15 percent, about 10 percent, about five percent, and about three percent) between any two, any three, any four, or even all pad sizes between the smallest size available for purchase and the largest size available for purchase as illustrated in Table II. Furthermore, the caliper of the core 22 may have substantially no variation (e.g., within 1 percent caliper) from one pad size to the next.

More broadly stated, as a pad size increases from a first size to a second size having a body-facing surface area between 5% and 40% greater than the body-facing surface area of the first size, the core thickness (or caliper) decreases by an amount less than about 50 percent (alternatively less than about 40 percent, about 35 percent, about 30 percent, about 25 percent, about 20 percent, about 15 percent, about 10 percent, about five percent, and alternatively still about three percent).

E. Odor Management

One or more of the above-described components of the incontinence pad 10, for example, the topsheet 16, backsheet 18, absorbent core 22, acquisition system 30, and/or core wrap 63, etc. may include a coating composition used to minimize odor caused from bodily fluids, for example, through a starch encapsulated accord (SEA) and a carrier. The SEA and carrier components can be present in a weight ratio of carrier to SEA of equal to or greater than 1:1. In one optional embodiment, the coating composition comprises from about 0 percent to about 10 percent by weight of coating composition of water, or any individual number within the range. In some embodiments, the coating composition comprises from about 0 percent to about 5 percent by weight of coating composition of water. In one specific embodiment, the coating composition is essentially free from water and contains only trace amounts of water. This low water content provides added stability and extended life to the SEAs, while also reducing manufacturing costs due to reduced product loss.

The coating compositions may comprise optional ingredients, such as but not limited to, aesthetic components, pigments and the like. Some illustrative optional ingredients are described herein. Desirably, at least an effective amount of the coating composition is applied to the article. Effective amounts are typically those which provide a noticeable scent signal to the consumer to signify the substrate on which the coating composition is attached has been contacted with sufficient aqueous fluid (e. g., menses, urine, etc.) or water containing solid (e.g., feces). In one optional embodiment, when the substrate is a part of a disposable absorbent article the typical amount of the coating composition present on the substrate is from about 0.001 g to about 5 g or any individual number within the range. In some embodiments, the amount of the coating composition present on the substrate can be from about 0.005 g to about 1 g, or more preferably from about 0.01 g to about 0.5 g, per substrate.

The coating compositions include starch encapsulated accords (SEAs). SEAs are solid particles comprising water-soluble cellular matrixes containing perfume stably held in the cells. In some embodiments, the SEAs may comprise perfume ranging from about 20 percent to about 60 percent by weight of the SEA or any individual number within the range. In some embodiments, the SEAs may comprise perfume from about 20 percent to about 50 percent by weight of the SEA.

In some embodiments, the SEAs may comprise mainly polysaccharide and/or polyhydroxy compounds, preferably from at least about 20 percent by weight of the SEA. In some embodiments, the SEAs may comprise from about 50 percent to about 80 percent by weight of the SEA. In some embodiments, the SEAs may comprise from about 20 percent to about 80 percent by weight of the SEA or any individual number within the range.

In some embodiments, the SEAs may comprise optional adjunct ingredients ranging from about 0 percent to about 5 percent, or any individual number within the range. Some suitable examples of adjunct ingredients include but are not limited to wetting agents, process aids, flow agent and the like and any combinations thereof. In some embodiments, the SEA may encapsulate a perfume.

As stated previously, in some embodiments, the SEAs may comprise mainly polysaccharide and polyhydroxy compounds. The polysaccharides can be higher polysaccharides of the non-sweet, colloidally-soluble types, such as natural gums, e.g., gum arabic, starch derivatives, dextrinized and hydrolyzed starches, and the like. The polyhydroxy compounds can be preferably alcohols, plant-type sugars, lactones, mono-ethers, and acetals.

The SEAs useful in the present invention can be prepared by forming an aqueous phase of the polysaccharide and polyhydroxy compound in proper proportions with added emulsifier if necessary or desirable, emulsifying the perfumes in the aqueous phase, and removing moisture while the mass is plastic or flowable (e.g., by spray drying droplets of the emulsion), in some embodiments. In one optional embodiment, it is desirable to have only minimal non-encapsulated surface perfume, more preferably of less than about 1 percent by weight of the SEAs.

In some embodiments, the SEAs can have a particle size of from about 0.5 μm to about 1000 μm, or any individual number within the range. In some embodiments, the SEAs can have an average particle size of from about 1 μm to about 300 μm, or any individual number within the range. In some embodiments, the SEAs may have an average particle size of from about 1 μm to about 500 μm and an average particle size of from about 1 μm to about 100 μm. In some embodiments, the SEAs can have a particle size of from about 1 μm to about 100 μm and an average particle size of from about 10 μm to about 50 μm. SEAs can be obtained commercially, e.g., as IN-CAP from Polak's Frutal Works, Inc., Middletown, N.Y.; and as Optilok System@ encapsulated perfumes from Encapsulated Technology, Inc., Nyack, N.Y. Other examples of suitable SEAs are available from Haarmann & Reimer, Teterboro, N.J. USA. The perfume ingredients and compositions may be conventional and well known in the art. Selection of any perfume component, or amount of perfume, can be based on functional and aesthetic considerations.

An example of an SEA is an IN-CAP microcapsule sample, obtainable from Polak's Frutal Works, Inc., having about 50 percent perfume loading and particle size range of from about 3 μm to about 100 μm. Major components of the perfume are highly volatile components, such as citral and d-limonene.

Typically, the SEA is present in the coating composition in an effective amount. An effective amount is that which is effective to provide for effective mixing of the SEA and carrier as well as to enable the coating composition to be delivered and attached to a substrate. In some embodiments, the SEA can be present in the coating compositions at levels from about 0.01 percent to about 99 percent by weight of the coating composition, or any individual number within the range. In some embodiments, the SEA can be present in the coating composition at levels from about 0.5 percent to about 97 percent, or preferably from about 1.0 percent to about 98 percent, by weight of the coating composition.

The coating compositions comprise a carrier, which may be capable of suspending the SEAs while having minimal or preferably no interaction with the SEAs which cause the perfume to be released. In some embodiments, the carrier is present in the coating compositions at levels from about 0.01 percent to about 99 percent by weight of the coating composition, or any individual number within the range. In some embodiments, the carrier can be present in the coating composition at levels from about 0.5 percent to about 97 percent, or preferably from about 1.0 percent to about 98 percent, by weight of the coating composition.

The carrier may be a liquid or it may be a solid which is a liquid at the temperature which the process is performed. In one optional embodiment the carrier is a polyalkylene glycol or mixtures thereof, such as polyethylene glycol, having a weight average molecular weights of from about 200 to about 20,000, from about 200 and about 10,000, from about 200 and about 7,500, or from about 400 and about 6,000 g/mole. Non-limiting examples of other suitable polyalkylene glycols include: polypropylene glycols, having weight average molecular weights of from about 600 to about 4,000 g/mole; poly(tetramethylene glycol), having molecular weights of from about 1,000 to about 10,000 g/mole; mixed polyalkylene glycols such as poly (ethylene oxide-propylene oxide or EO/PO) glycol having a weight average molecular weight of about 1,100 g/mole, and an EO/PO ratio of about 0.15:1; a poly (ethylene oxide-propylene oxide) glycol having a weight average molecular weight of about 3,440 g/mole, EO/PO ratio of about 0.33:1; a poly (ethylene oxide-propylene oxide) glycol having a weight average molecular weight of about 2,920 g/mole, EO/PO ratio of about 0.8:1; a poly (ethylene oxide-propylene oxide) glycol having a weight average molecular weight of about 13,333 g/mole, EO/PO ratio of about 3:1; and a poly (ethylene oxide-propylene oxide) glycol having a weight average molecular weight of about 8,750 g/mole, EO/PO ratio of about 5:1; and mixed polyalkylene glycol block copolymers such as HO—[CH2CH20] x-[CH2CH (CH3)O]y-[CH2CH20],-H and/or HO—[CH (CH3)CH2O] y-[CH2CH2O] X—[CH2CH (CH3)O] y-H wherein the sum of the y's ranges from about 15 to about 70, and the ratio of the sum, of the x's to the sum of the y's is from about 1:10 to about 11:10, more preferably from about 1:2 to about 1:1. Commercially available examples of these materials include materials made by BASF Corporation and sold under the trade names of Pluronic and Pluronic R surfactants, respectively.

Other examples of suitable carriers include the Ci-C22, preferably C1-C4 alkylated polyalkylene glycols [poly (alkylene glycol) mono- and dialkyl ethers], RO—(R2O) n-H and/or RO—(R2O) n-R, with each R being methyl, ethyl, propyl, or butyl; each R2 being a C2-C4 alkylene group; and n ranging from about 1 to about 200, with the percentage of polyalkylene glycol being preferably more than about 50 percent.

Specific examples include: RO—[CH2CH (CH3)O] m-H, with R being methyl, ethyl, propyl, or butyl; and m being from 1 to about 200; RO—(CH2CH2O) n-H, with each R being methyl, ethyl, propyl, or butyl, methyl; and n being from about 2 to about 200, from about 15 to about 150, from about 15 to about 100; and/or RO—(CH2CH20) n-R, with each R being methyl, ethyl, propyl, or butyl; and n being from about 2 to about 200, from about 15 to about 150, or from about 15 to about 100.

Other suitable carriers include Polyalkoxylated materials having a weight average molecular weight of from about 200 to about 20,000 g/mole and the weight percent of the polyalkoxy portion being from about 50 percent to about 99 percent. Specific examples include: Tetronic and TetronicRO; and Varstat66 (D. TekonicW and TetronicRW are block copolymeric surfactants, manufactured by BASF Corporation. Varstat66 is sold by Sherex Chemical Company.

In one optional embodiment, the carrier may be an oil, which is liquid or in the molten phase at the temperature which the process is performed (i.e., a solid which is liquid at temperatures at which the process is to be performed). Examples of suitable oils include but are not limited to, mineral oil, light oil, white mineral oil, vaseline, liquid petroleum, petrolatum, petrolatum gel and combinations thereof. Other materials suitable for use as carriers include, but are not limited to, polyols such as glycerine/glycerol/glycerin (1,2,3-Propanetriol), paraffin waxes, fatty alcohols, such as but not limited to stearyl alcohol and the like, and combinations thereof. In another optional embodiment, the carrier is selected from the group consisting of polyalkylene glycols, preferably polyethylene glycols, alkoxylated nonionic surfactants, mineral oil, polyols, paraffin waxes, and combinations thereof. In another optional embodiment, the carrier is a polyethylene glycol having a weight average molecular weight of from about 100 to about 10,000, more preferably from about 200 to about 7,500 g/mole. Carrier may include a mixture of possible carriers.

Regardless of which carrier is to be used, the carrier should be compatible with the SEA and suitable for the intended use of the substrate to which it is attached. For example if the substrate is to be incorporated into the topsheet 16, the carrier needs to be compatible for use in the incontinence pad 10.

The weight ratio of the carrier to the SEA may be equal to or greater than about 1:1, preferably from about 1:1 to about 10:1, even more preferably from equal to or greater than about 1:1 to about 5:1. It has been surprisingly found that this ratio is critical to ensure the even suspension of the SEA in the carrier as well as improving the processability, delivery and attachment of the coating composition to a substrate. This relative relationship (i.e., the ratio, between the carrier and SEA) provides a coating composition which is easy to process and provides simple delivery and good attachment to the substrate. The relationship between the carrier and SEA also allows for effective delivery of the optimal amount of SEA to a substrate thereby producing cost savings in raw materials, and reducing losses of SEA during the various process steps. The coating compositions are highly processable allowing for efficient and simplified delivery of the SEA, in the coating composition, to the substrate. For example, since the coating composition is readily processable, the SEAs can be accurately targeted for deposition onto a substrate (e.g., the deposition of the coating composition can be easily limited to one or more regions on the substrate without coating the entire substrate). This is an additional cost saving as the targeted deposition of SEA means it is possible to reduce the amount of SEA necessary, thereby further reducing costs.

The coating compositions may optionally contain one or more optional ingredients. Examples of these ingredients include, but are not limited to: aesthetic components, pigments, colorings, colorants, anti-caking agents, antifoaming agents, preservative, dye, antimicrobial agents (e.g., quaternium-15, methyl paraben, ethyl paraben, propyl paraben, DMDM hydantoin, Suttocide A, IPBC, etc.), antioxidants, fluorescence agents, binders, fumed silica, biological additives, buffering agents, bulking agents, chelating agents, chemical additives, solvents (other than water), cosmetic biocides, denaturants, humectants, opacifying agents, pH adjusters, process aids, reducing agents, sequestrants, binders, thickeners, hydrocolloids, zeolites, and the like.

Optional ingredients, when present, are each typically employed in compositions at levels of from about 0.0001 percent to about 99.9 percent by weight of the coating composition, or any individual number within the range. In some embodiments, the optional ingredients may be present in the composition at levels from about 0.001 percent to about 99 percent, or preferably from about 0.01 percent to about 97 percent, by weight of the coating composition.

F. Visual Indicia

Figure 18:
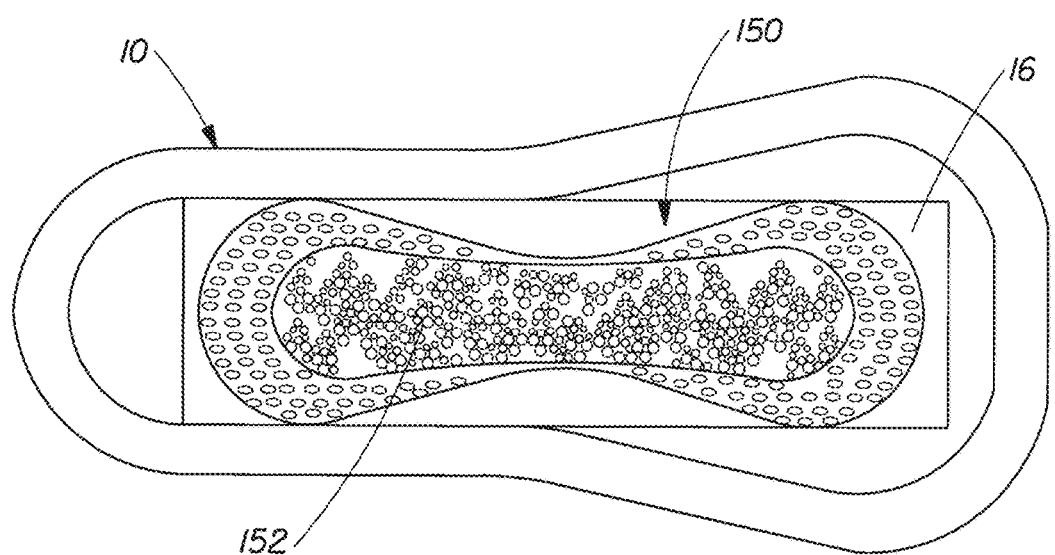
FIG. 18 is a top plan view of an embodiment of an incontinence pad including indicia with the body-facing surface of the pad facing the viewer.
Figure 19:
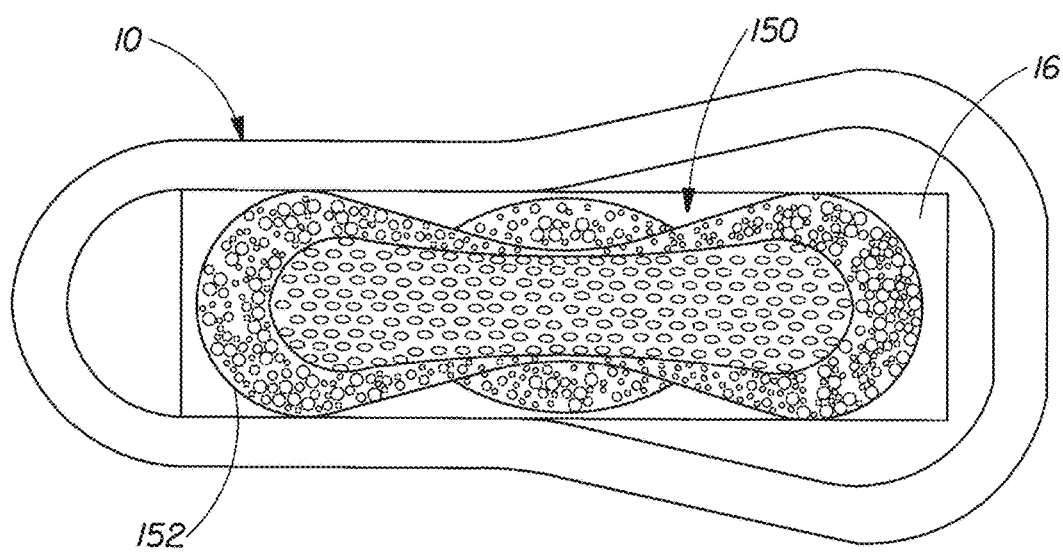
FIG. 19 is a top plan view of another embodiment of an incontinence pad including indicia with the body-facing surface of the pad facing the viewer.
Figure 20:
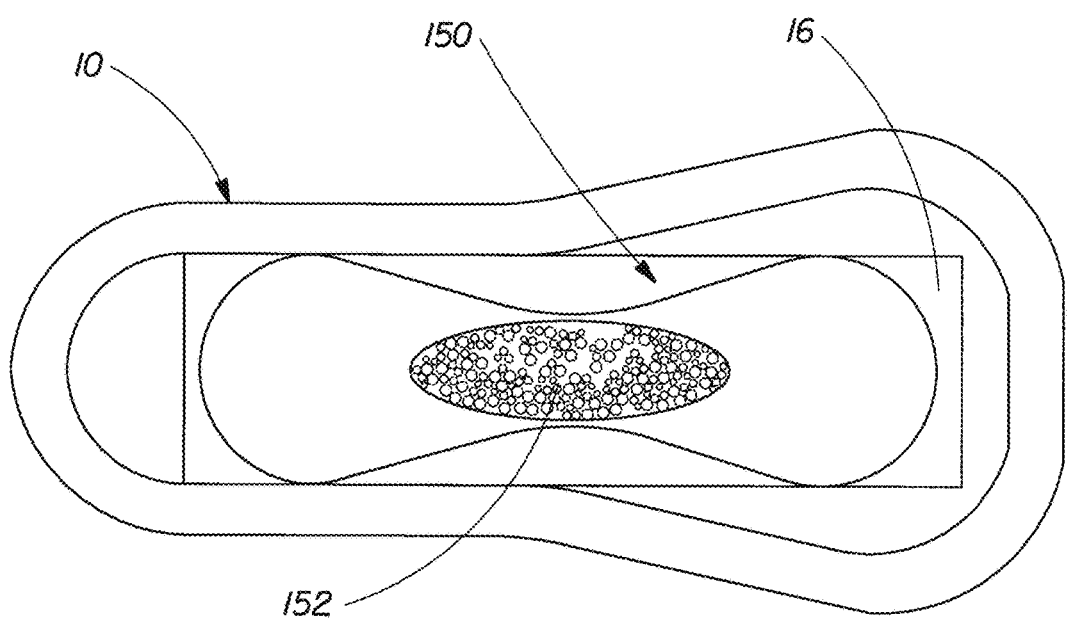
FIG. 20 a top plan view of another embodiment of an incontinence pad including indicia with the body-facing surface of the pad facing the viewer.

Referring to FIGS. 18-20, incontinence pad 10 may include indicia 150 that are visible or at least partially visible through topsheet 16. The indicia 150 may be printed on any layer where the indicia is at least partially visible through the topsheet 16, such as on the lower surface of the topsheet 16 opposite the body-facing portion and/or on the upper surface of the acquisition system 30 facing the body-facing portion.

In some embodiments, indicia 150 may comprise a graphic that includes colors such as violet, blue, lavender, white, and/or any other suitable color and/or illustrations such as a pattern, for example, of speckles or dots 152 that indicates an effective quality of the incontinence pad 10. Without wishing to be bound by theory, it has been observed that female incontinence pad users identify certain colors such as lavender as indicating an absorptive quality and certain patterns such as speckles as indicating an odor management quality.

Referring to FIGS. 21 and 22, an embodiment is shown where incontinence pad 10 is secured in a folded configuration, for example, for packaging. Incontinence pad 10 has a wrapping sheet 300 affixed thereto using the adhesive of adhesive region 202. The wrapping sheet 300 can be removed from the adhesive region 202 to expose the adhesive region 202 for use. In the illustrated example, incontinence pad 10 is folded in a tri-fold configuration having three lateral portions 302, 304 and 306. Other folding configurations are contemplated. A releasable fastener 308, such as releasable tape, secures the incontinence pad 10/wrapping sheet 300 in the folded configuration.

Wrapping sheet 300 is releasable from the adhesive region 202. Referring to FIG. 23, in some embodiments, the wrapping sheet 300 may include an outer layer 310 (e.g., a non-woven material), an intermediate, bonding layer 312 (e.g., polyethylene) and an inner layer 314 (e.g., silicon). Referring to FIG. 24, as an alternative, wrapping sheet 300 may include an outer layer 310 (e.g., a non-woven material) and an inner layer 318 formed of a release paper that is bonded to the outer layer 310.

G. Reinforcement Elements

Figure 25A:
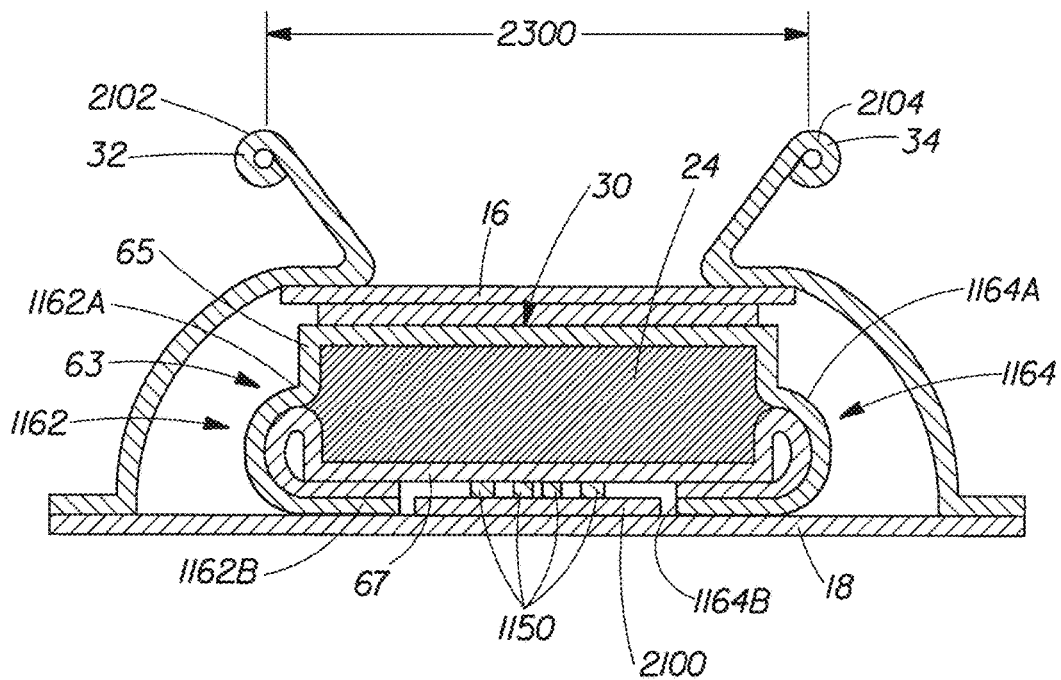
FIG. 25A is a section view of another embodiment of an incontinence pad including a reinforcement element.
Figure 25B:
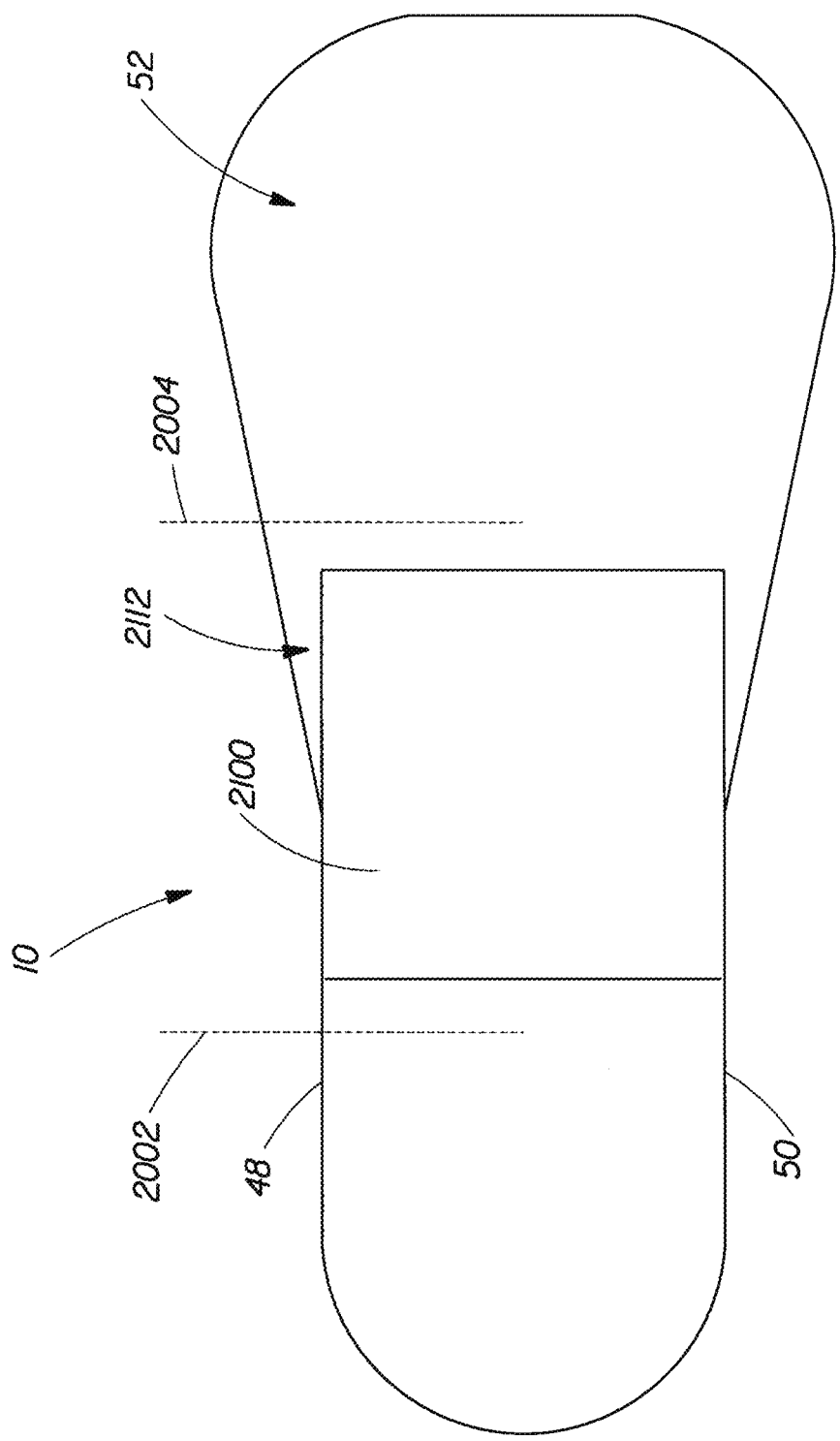
FIG. 25B is a plan view showing the garment-facing surface of an incontinence pad constructed in accordance with the present invention.

Referring to FIGS. 25A and 25B, in some embodiments, the incontinence pad 10 may further comprise a reinforcement element 2100. The reinforcement element 2100 can be utilized in any of the embodiments discussed herein. As shown, the reinforcement element 2100 is utilized in an article similar to that described in FIG. 11B.

As shown in FIG. 25A, in some embodiments, the reinforcement element 2100 may be disposed between the topsheet 16 and the backsheet 18. Specifically, in the embodiment shown, the reinforcement element 2100 may be disposed between the core cover 63 and the backsheet 18. The core cover 63 may be bonded to the reinforcement element 2100 via adhesive elements 1150. Embodiments are contemplated where the reinforcement element is disposed between the topsheet 16 and the storage layer 24.

Additionally, embodiments are contemplated where the reinforcement layer 2100 is disposed on a garment-facing surface of the backsheet 18. In this specific embodiment, adhesive may be applied to the reinforcement element 2100 and other portions of the garment-facing surface of the incontinence pad 10 such that the incontinence pad 10 can be joined to an undergarment.

The reinforcement element 2100 of the present invention may assist in keeping the barrier leg cuffs 32 and 34 spaced apart. As shown in FIG. 25A, the barrier leg cuff 32 includes an upstanding edge 2102, and the barrier leg cuff 34 includes an upstanding edge 2104. The reinforcement element 2100 can assist in maintaining a distance 2300 between the upstanding edge 2102 and the upstanding edge 2104. In embodiments comprising a reinforcement element 2100, the distance 2300 can be between about 40 mm to about 90 mm or any individual number within the range. In some embodiments, the distance can be between about 55 mm to about 75 mm.

As shown in FIG. 25B, the incontinence pad 10 is shown in a flat configuration with the garment-facing surface 52 facing towards the viewer. As shown, in some embodiments, the reinforcement element 2100 can be disposed within an area 2112 between a first fold line 2002 and a second fold line 2004 of the incontinence pad 10. The area 2112 can be bounded by the first fold line 2002 and the second fold line 2004 as well as the side edges 48 and 50. The reinforcement element 2100 can be disposed within the area 2112 in some embodiments. Additionally, in some embodiments, the reinforcement element 2100 can be bounded by the first fold line 2002 and/or the second fold line 2004 and/or the side edge 48 and/or side edge 50.

The reinforcement element 2100 of the present invention may comprise any suitable material known in the art. For example, the reinforcement element 2100 may comprise a material made from polyethylene, polypropylene, polyethylene teraphthalate, rubber, urethane, cellulose, or any suitable combination thereof. In a specific embodiment, the reinforcement element 2100 may comprise a nonwoven having polyethylene teraphthalate fibers having resin bonds. In another embodiment, the reinforcement element 2100 may comprise a material which is similar to the material of an acquisition layer described heretofore.

One benefit of the reinforcement element 2100 as shown in FIG. 25B is that the folds along the fold lines 2002 and 2004 have a reduced thickness compared to the thickness which would occur if the reinforcement element 2100 extended the length of the incontinence pad 10. Additionally, a reinforcement element 2100 extending the full length of the incontinence pad 10 may cause wearer discomfort. Still another benefit is that the reinforcement element 2100, as shown in FIG. 25B, can help hold the incontinence pad 10 open, e.g., maintain the distance 2300, in the general middle of the incontinence pad 10. Holding the incontinence pad 10 open can reduce the likelihood of leakage from the pad 10.

Figure 33:
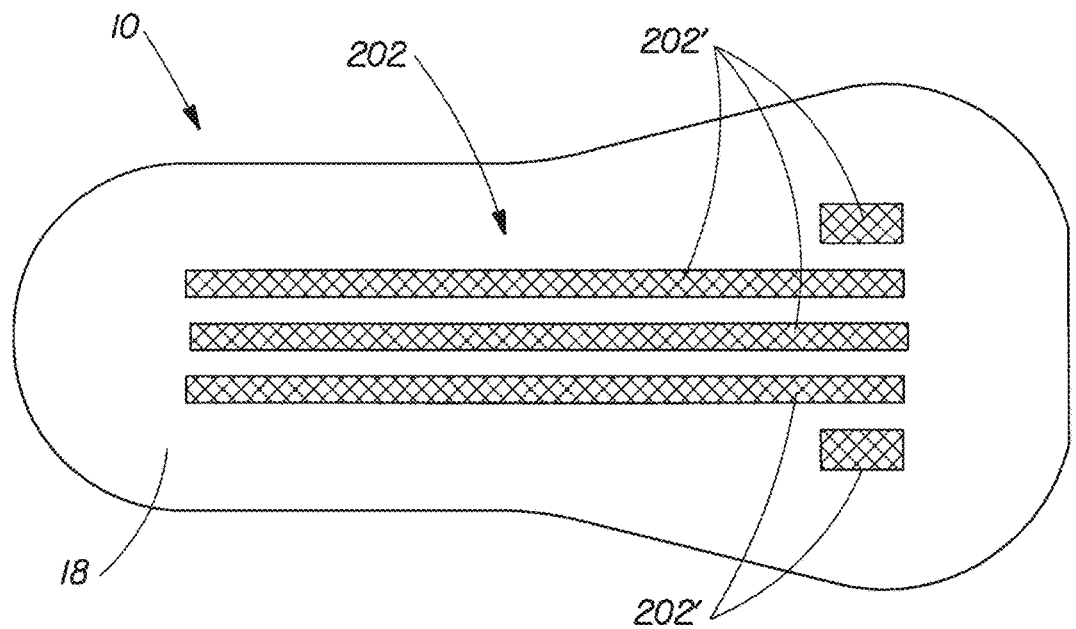
FIG. 33 is a plan view of another embodiment of an incontinence pad.
Figure 34:
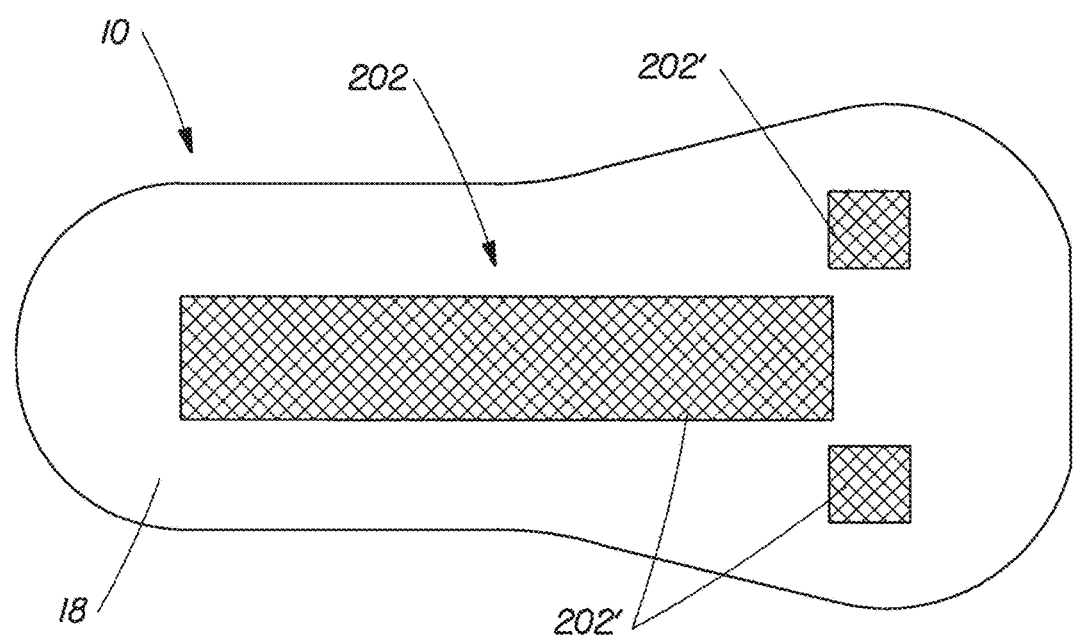
FIG. 34 is a plan view of another embodiment of an incontinence pad.

A number of detailed embodiments have been described. Nevertheless, it will be understood that various modifications may be made. For example, referring to FIGS. 33 and 34 adhesive region 202 can be formed from multiple, spaced-apart regions 202'. In some embodiment, the adhesive region 202 shape is substantially similar to the pad shape and/or the core shape. Accordingly, other embodiments are contemplated. Further embodiments are contemplated including elements of the embodiments presented herein in any suitable combination.

H. Tests

Peel Strength

Peel strength is measured on a constant rate of extension tensile tester with computer interface (a suitable instrument is a MTS Synergie 200 under TestWorks 4 software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips, wider than the width of the test specimen.

For analysis, the specimen is mounted in the device detailed in FIGS. 28A and 28B. The device consists of a rigid steel mounting plate 262 (253 mm long by 82 mm wide by 1.5 mm thick; 2700, 2701 and 2702 respectively) with a raised center region (177 mm long by 70 wide by 7.3 thick; 2703, 2704 and 2705 respectively). The specimen is securely held in place using a plastic friction grip frame 264 (226 mm long by 83 mm wide by 5.8 mm thick; 2710, 2711 and 2712 respectively) with a cut-out region (178 mm long by 71 mm wide; 2713 and 2714 respectively), as detailed in FIGS. 28C and 28D. The cut-out is pressed down around the raised surface of the steel plate 262 and sandwiches the specimen between the steel plate 262 and the friction grip frame 264.

Figure 26:
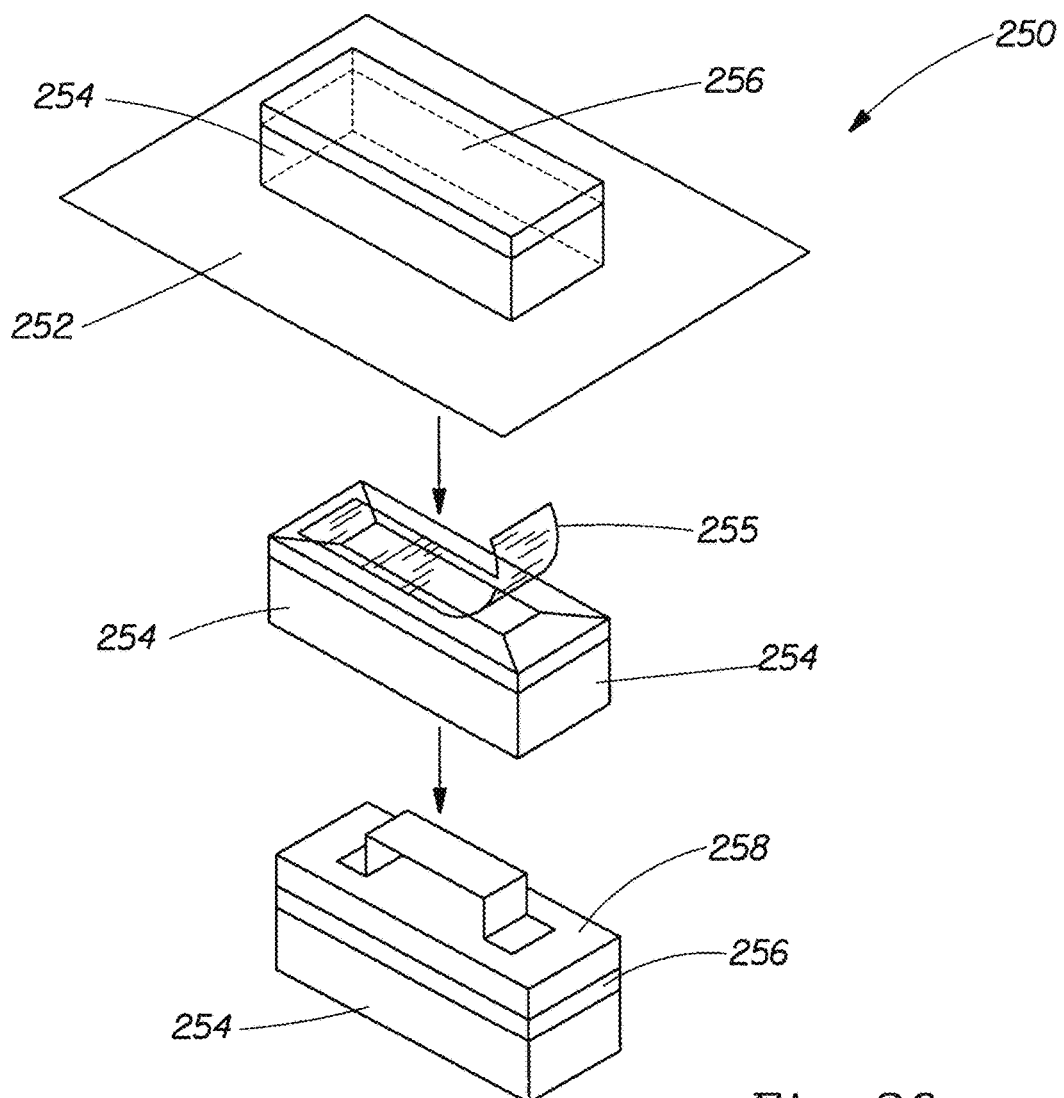

A foam-padded weight 250 is constructed as shown in FIG. 26, by laying a polyethylene film 252 (250 mm long by 150 mm wide by 25 μm thick) flat on a bench surface. A piece of polyurethane foam 254 (140 mm long by 57 mm wide by 25 mm thick; available from Concord-Renn Co. Cincinnati, Ohio, density of 1.0 lb/ft3, IDL 24 psi) is laid centered on top of the film. A piece of Plexiglas 256 (140 mm long by 57 mm wide by 6.4 mm thick) is then stacked on top of the polyurethane foam. Next the polyethylene film 252 is used to wrap the polyurethane foam and Plexiglas plate securing it with transparent tape 255. A metal weight with handle 258 (140 mm long by 57 mm wide) is stacked on top of, and fastened to, the Plexiglas plate. The mass of the metal weight 258 is chosen such that the total weight of the constructed foam-padded weight 250 is 4.14 Kg.

Figure 27:
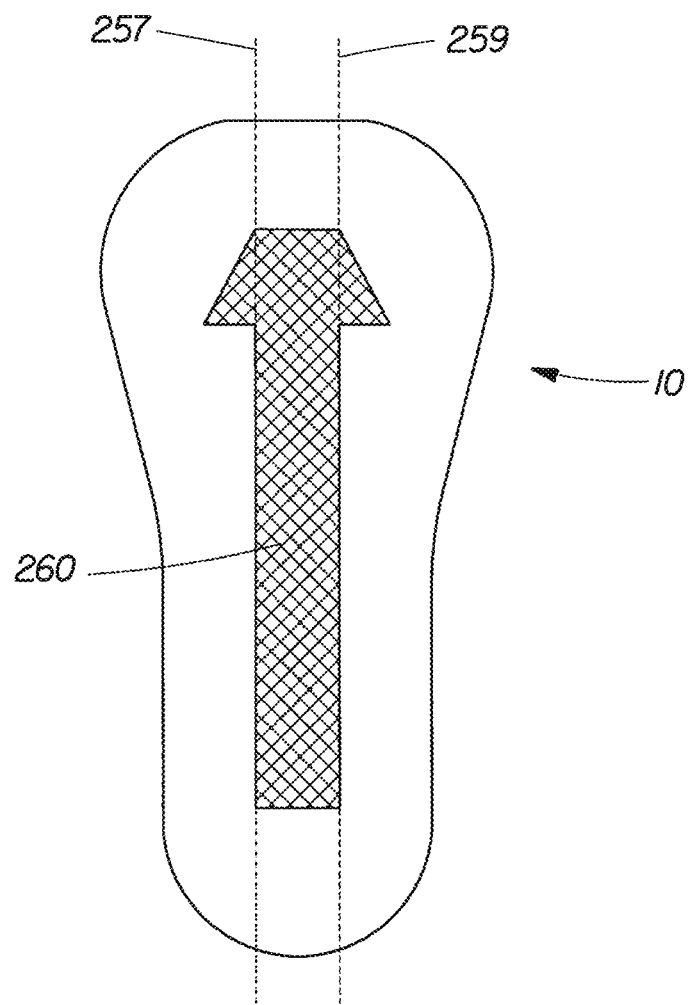

Place the sample article, topsheet down, on a flat bench. Measure and mark the width of the adhesive zone which extends down the center longitudinal axis of the article (lines 257 and 259 as shown in FIG. 27). This zone can consist of a single adhesive strip, a plurality of strips, or any other adhesive pattern. Adhesive regions outside of the central longitudinal zone are not included as part of the test specimen (e.g., triangle regions outboard of lines 257 and 259). Cut a specimen strip 260 the entire length of the article along lines 257 and 259, and remove the core and topsheet. Allow the specimen to equilibrate to room temperature for 10 minutes before proceeding.

Figure 29:
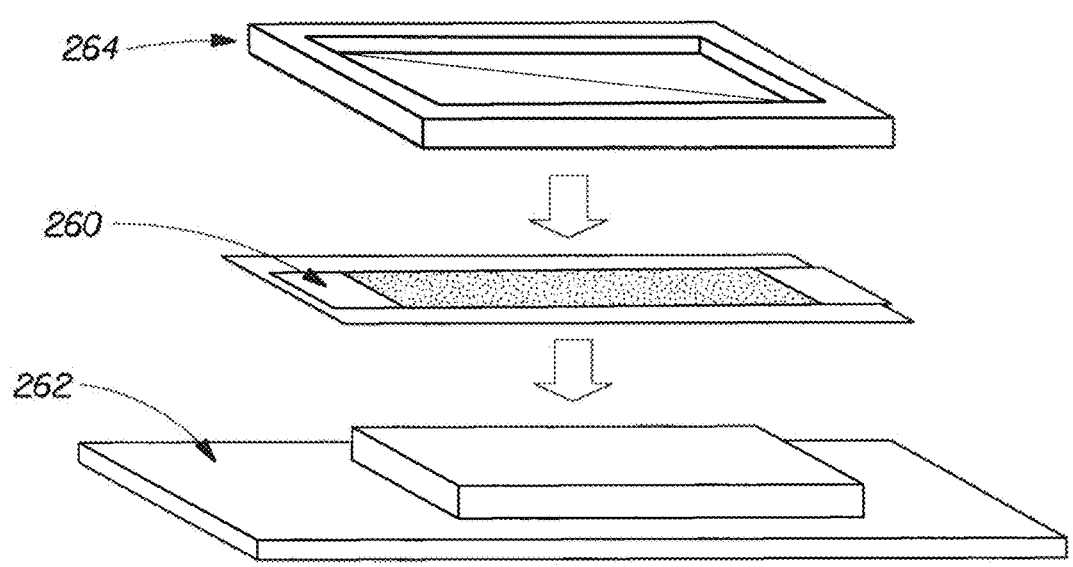

Place the specimen 260 centered longitudinally and laterally onto the steel mounting plate 262. As shown in FIG. 29, the plastic friction grip frame 264 is pressed down over the raised portion of the mounting plate 262 to sandwich the specimen 260 between the frame 264 and the steel plate 262. After the specimen 260 is secure, remove the release paper.

Figure 30:
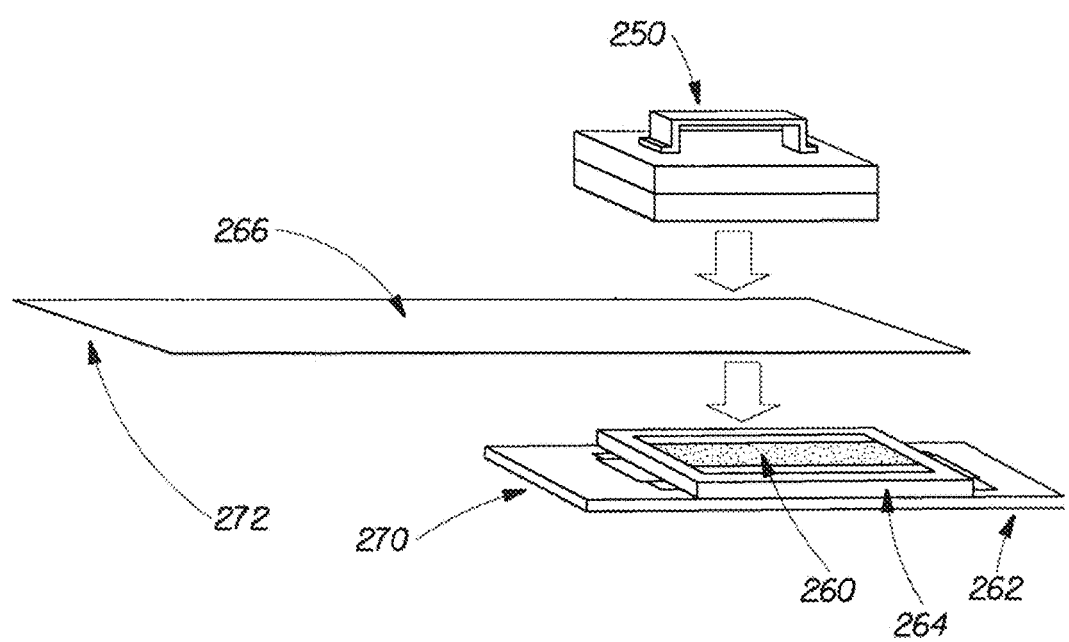

Referring to FIG. 30, lay a 457 mm long by 76 mm wide standard cotton swatch 266 (white, 100% cotton weave, style #429-W available from Test Fabrics, Inc. Middlesex, N.J.) over the assembled mounting device. The cotton swatch 266 should extend the length of the friction frame cut-out with an additional 25 mm or more extending past the top of the frame. Gently and evenly place the foam-padded weight 250, on the specimen as shown in FIG. 30. The weight should cover the specimen completely. The weight remains on the specimen for 30 seconds and then removed.

Figures 31A, 31B:
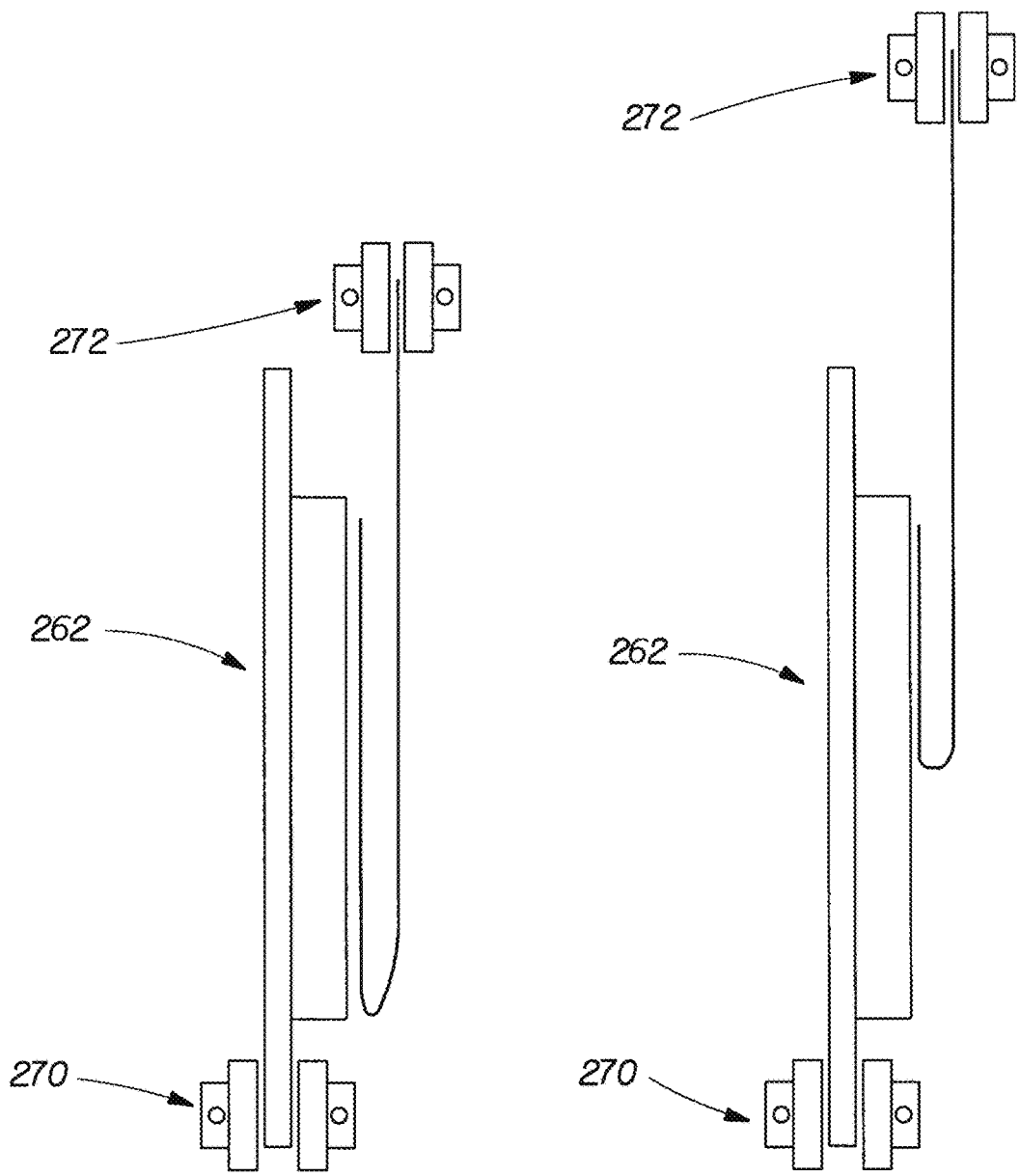

Less than 1 minute after removing the weight, place the bottom of the steel plate 262 (labeled 270 in FIG. 30) into the lower, stationary jaw of the tensile tester, and close the grip faces. Fold the long end (labeled 272 in FIG. 30) of the cotton swatch 266 back over itself and place into the upper, movable jaw and close the grip faces. FIGS. 31A and 31B depict the proper configuration for the test. Start the tensile tester and data collection. The jaws are moved apart at an initial rate of 1016 mm/min until the cotton swatch is detached from the specimen. The software is used to calculate the average Peel Force (N) between 58 mm and 170 mm from the resulting force/extension curve and reported to the nearest 0.1 N.

Density/Caliper/Basis Weight Measurement

The caliper of a test specimen is measured using a digital caliper (a suitable instrument is model # GS-503 available from Ono Sokki). The foot has a diameter 4 cm with the anvil at least 2 cm larger in diameter than the foot. The mass of the foot is chosen to apply a pressure of 1.25 kPa. The specimen is placed between the foot and anvil and a reading is taken after pressure has been applied for 5 seconds. The thickness should be reported to the nearest 0.01 mm as the average of three replicates.

The basis weight is determined in the typical fashion. Conveniently, a 10 cm by 10 cm of the specimen is accurately cut to the closest 0.5 mm and weighed on an analytical balance to the nearest 0.001 g. Basis weight can then be calculated from the mass and specimen area, and reported as $g/m^2$. From the basis weight and caliper measurements, the density can be calculated and reported as $g/m^3$.

These measurements should be repeated on at least three specimens taken from the same sample, and reported as the average value.

Wet Immobilization Measurement

Figure 32:
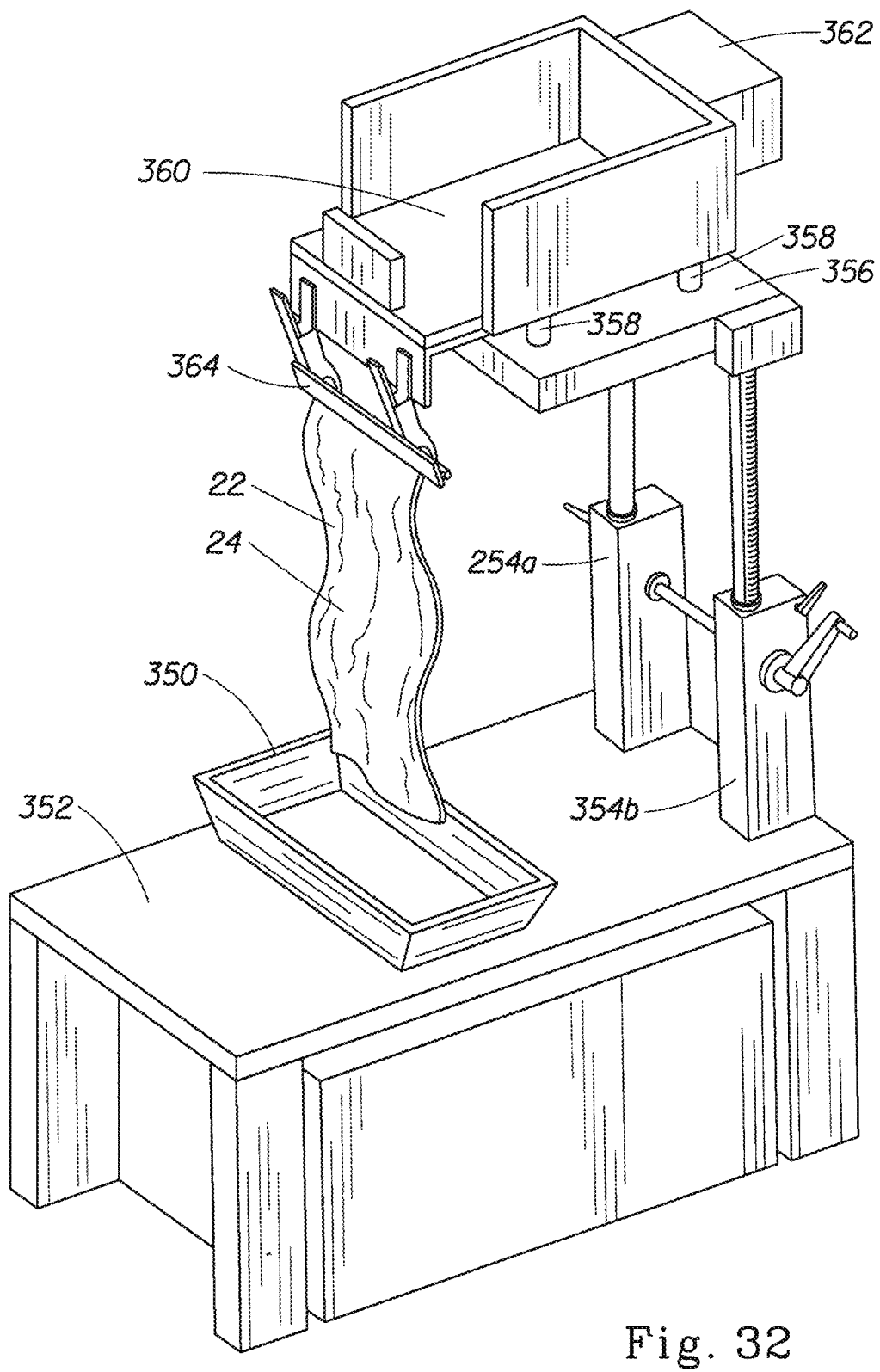
FIG. 32 illustrates a method and apparatus for testing wet immobilization.

The wet immobilization test is performed using a shaking device as described herein and shown in FIG. 32. Ten absorbent articles are analyzed for each test and the wet immobilization value is reported as the average. Prior to testing, the percent of Super-Absorbent Polymer (SAP) contained in the sample, and the Centrifuge Retention Capacity (CRC) of that SAP must be measured.

The shaker comprises a base 352, a height adjustable support platform 356, and a vibration table 360. The base 352 is of sufficient size and weight to provide stable shaking conditions. The support platform 356 is mounted onto the base 352 with two height adjustable legs 354a and 354b, which are adjusted to accommodate the specific height of the specimen to be tested. The vibration table 360 is mounted via rubber supports 358 to the platform 356. The table 360 consist of a tray structure from which the specimen can be hung vertically from a rigidly attached clamp 364 (dimensions: 1 inch by wider than the specimen), and an electric motor 362. The motor 362 shakes the vibration table at a frequency of 16.8 Hz with a vertical amplitude of 4 mm and a horizontal amplitude of 1 mm relative to the support plate 356.

Prepare a specimen by removing all layers of the absorbent article that do not directly wrap the SAP containing core (e.g., topsheet, backsheet, and any acquisition layers that do not contain SAP). Care must be taken while removing the layers not to disturb the integrity of the core. Measure the length of the core along its longitudinal axis to the nearest 1 mm, and calculate an inset that is 5% of the overall length. Measure this inset distance along the longitudinal axis of the core, starting from its top edge, and draw a transverse line across the width at that point. Repeat from the bottom edge of the specimen. Cut the core along both lines, to yield the test specimen. Measure and record the mass of the dry specimen ($M_{dry}$) on an analytical balance to the nearest 0.1 g.

The test solution used to wet the specimen is 0.9% (w/w) saline solution that is heated to 37° C. The volume of test solution added is based on 50% of the capacity of the SAP present in the specimen and is calculated as $$M_{dry} \times \frac{\%SAP}{100} \times CRC \times 0.50$$

and converted to mL based on a density of 1 g/mL.

Lay the specimen flat into a tray 350 (10 mm deep by about 10% greater than the size of the core), and slowly pour the calculated volume of test solution onto the center of the pad. Allow to equilibrate for 5 minutes and measure the wet specimen mass (M1) on an analytical balance to the nearest 0.1 g.

Securely attach the top edge of the specimen to the vibration table 360 by placing 20 mm of the specimen into the clamp 364. Adjust the height of the support platform so that the bottom free end of the specimen is 40 mm above the base as it hangs vertically. For convenience, place the tray 350 under the specimen to catch core material that falls from the specimen. Start the motor 362 and shake the specimen for 80 seconds. Next, remove the specimen from the clamp 364, and place the opposite end of the specimen into the clamp. If necessary, carefully reopen the free end if it was sealed close from the pressure of the clamp during the previous shaking step. Allow the specimen to again hang vertically and start the motor to shake the specimen for an additional 80 seconds. Remove the specimen from the clamp and remeasure its mass (M2) to the nearest 0.1 g.

Calculate the Wet Immobilization Value (%) as $$\frac{(M1 - M2)}{M1} \times 100$$

for each of ten replicates and report the average to the nearest 1%.

Centrifuge Retention Capacity (CRC) Method

The Centrifuge Retention Capacity (CRC) test is a measure of the retention of liquids by a SAP. The SAP is placed within a "tea bag" immersed in a 0.9% (w/w) sodium chloride solution for 30 minutes, and then centrifuged for 3 minutes. The ratio of the retained liquid weight and the initial weight of the dry material is the CRC (g/g) of the SAP. The CRC test is performed under standard laboratory conditions of 23° C.±2° C. and 50%±2% relative humidity.

The teabag pouch is made from a 6 cm by 12 cm piece of tea bag material (grade 1234 heat sealable material, available from the Dexter Corporation, Windsor Locks, Conn., or equivalent) that is folded in half lengthwise and sealed along two sides with a T-bar sealing device.

Accurately weigh 0.200 g±0.005 g of SAP particles into a tea bag pouch and seal the third (open) side. Seal an empty pouch to use as a blank. Pour approximately 300 mL of 0.9% saline into a 1000 mL beaker and submerge the blank tea bag into the saline. Hold the sample tea bag horizontally to distribute the particles within the tea bag. Lay the sample tea bag on the surface of the saline solution; then, using a spatula, submerged for about 5 seconds to wet the sample. Soak the blank and sample tea bags for 30 minutes. A second replicate, both sample and blank, is performed in parallel in like fashion.

After 30 minutes, promptly remove the tea bags and place into a centrifuge (a suitable instrument is the Delux Dynac II Centrifuge from Fisher Scientific, fitted with a 22 cm diameter, circular centrifuge basket). Space the replicate samples in the basket to balance the centrifuge. Start the centrifuge and allow it to quickly ramp up to a stable speed of 1500 rpm (250 g). After 3 minutes at 1500 rpm, turn the centrifuge off and apply the brake. Remove the tea bags and immediately measure the mass of each teabag and record to the nearest 0.001 g.

The CRC is calculated as $$\frac{(Mass_{sample\ tea\ bag} - Mass_{blank\ tea\ bag} - Mass_{dry\ SAP})}{Mass_{dry\ SAP}}$$

and is reported as the average value of the two replicates to the nearest 0.01 g/g.

% Super Absorbent Polymer Method

SAPs distributed through out a SAP/cellulose fiber core can be quantified based on the following concept. Neutralized or partially neutralized polyacrylate based SAPs can be suspended in a aqueous system and converted to the acid form by reaction with a strong acid such as hydrochloric acid. If the acid form of the polymer is then removed from the suspension, the reduction of hydrogen ions in the remaining aqueous system can be taken as a measure of the amount of neutralized or partially neutralized SAP originally present.

Prepare a specimen by removing all layers of the absorbent article that do not directly wrap the SAP containing core (e.g., topsheet, backsheet, and any acquisition layers). Measure the mass of the specimen on an analytical balance to the nearest 0.01 g. Cut the specimen in half and add both pieces to a known volume of standardized hydrochloric acid. Mix the test specimen for 20 minutes using common mixing equipment. Remove a portion of the suspension and filter it through Whatman #4 filter paper. Titrate an aliquot of the filtrate with standardized sodium hydroxide to a bromophenol blue endpoint (pH 4.5). Also titrate an acid blank in like fashion. Normality of the standardized acid and base solutions are adjusted based on the amount of SAP to be titrated. For example a specimen containing 10 g of SAP could be diluted in 1 Liter of 0.1 N HCl, and a 50 mL filtered aliquot titrated with 0.1 N NaOH.

Using a SAP compositionally identical to that found in the absorbent article to be tested (this can be SAP from the production run or SAP harvested from a second core by mechanical manipulation), create a calibration curve of mass of dry SAP verses the volume of NaOH titrated. Calculate the blank corrected amount of SAP from the calibration curve and ratio it to the mass of the original specimen. Report the % SAP (g/g) to the nearest 0.1%.

End of Test Methods

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article for wearing about the lower torso of a wearer, the absorbent article having a first region, a second region, and a crotch region disposed between the first and the second region, a longitudinal axis and a lateral axis, the absorbent article further comprising:
    a topsheet;
    a backsheet joined to at least a portion of the topsheet, said backsheet having a garment-facing surface, said garment-facing surface having an adhesive region having an adhesive material disposed thereon;
    a reinforcement element wherein the reinforcement element consists of a nonwoven having polyethylene teraphthalate fibers having resin bonds; and
    an absorbent core disposed between the topsheet and the backsheet, wherein the absorbent core comprises:
        a first acquisition layer having a first acquisition shape;
        a storage layer having a storage layer shape, the storage layer comprising a substrate layer, a cover layer, a thermoplastic composition, and an absorbent polymer material; and
        a core cover having a top layer and a bottom layer, the storage layer being at least partially disposed between the top layer and the bottom layer,
    wherein the storage layer comprises less than 20 percent airfelt; wherein the first acquisition shape is different from the storage layer shape; and
    wherein the reinforcement element is disposed only within an area located between a first fold line and a second fold line of the absorbent article, wherein the first fold line and the second fold line parallel the lateral axis, wherein the first fold line bisects the longitudinal axis at between 25 and 40% of the length of the longitudinal axis as measured from a front edge, and wherein the second fold line bisects the longitudinal axis at between 60 and 75% of the length of the longitudinal axis as measured from the front edge.

2. The absorbent article of claim 1 wherein a surface area of the first acquisition layer is greater than at least 50% of a surface area of the storage layer.

3. The absorbent article of claim 1 wherein the first acquisition layer has a first width in the first region and a second width in the second region, and wherein the first width is less than the second width.

4. The absorbent article of claim 1 further comprising a second acquisition layer having a second acquisition shape, wherein the second acquisition layer is in fluid communication with the first acquisition layer.

5. The absorbent article of claim 4 wherein a surface area of the first acquisition layer and/or a surface area of the second acquisition layer is at least as much as a surface area of the storage layer.

6. The absorbent article of claim 4 wherein the first acquisition shape and the second acquisition shape are different.

7. The absorbent article of claim 1 further comprising a fold structure capable of unfolding to accommodate the expansion of the storage layer and wherein the core cover comprises the fold structure.

8. The absorbent article of claim 7 wherein the fold structure includes a proximal area and a distal area, wherein the proximal area is disposed adjacent to the first storage layer and/or second storage layer and the distal area is disposed between the core cover and the backsheet.

9. The absorbent article of claim 1 further comprising a fold structure capable of unfolding to accommodate the expansion of the storage layer, and wherein the backsheet comprises the fold structure.

10. The absorbent article of claim 1, wherein the absorbent article comprises a dual layered barrier leg cuff.

11. The absorbent article of claim 1, wherein the first fold line is located at about 33% of the total distance of the longitudinal axis from the front edge and wherein the second fold line is located at about 33% of the total distance of the longitudinal axis from a back edge.

* * * * *